(12) United States Patent
Yamashita et al.

(10) Patent No.: US 11,731,930 B2
(45) Date of Patent: Aug. 22, 2023

(54) PROCESSES FOR PREPARING A (1,2-DIMETHYL-3-METHYLENECYCLOPENTYL)ACETATE COMPOUND AND (1,2-DIMETHYL-3-METHYLENECYCLOPENTYL)ACETALDEHYDE

(71) Applicant: Shin-Etsu Chemical Co., Ltd., Tokyo (JP)

(72) Inventors: Miyoshi Yamashita, Joetsu (JP); Takeru Watanabe, Joetsu (JP); Takeshi Kinsho, Joetsu (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 17/805,525

(22) Filed: Jun. 6, 2022

(65) Prior Publication Data

US 2023/0002305 A1 Jan. 5, 2023

(30) Foreign Application Priority Data

Jun. 9, 2021 (JP) ................. 2021-096743

(51) Int. Cl.
| | | |
|---|---|---|
| *C07C 67/14* | (2006.01) | |
| *C07C 45/67* | (2006.01) | |
| *C07C 29/147* | (2006.01) | |
| *C07C 45/41* | (2006.01) | |

(52) U.S. Cl.
CPC ............ *C07C 67/14* (2013.01); *C07C 29/147* (2013.01); *C07C 45/41* (2013.01); *C07C 45/67* (2013.01)

(58) Field of Classification Search
CPC ......... C07C 67/14; C07C 45/41; C07C 45/67; C07C 29/147
See application file for complete search history.

(56) References Cited

PUBLICATIONS

Mori, K., Pheromone synthesis. Part 260: Synthesis of (+-)-(anti-1,2-dimethyl-3-metylenecyclopetyl)acetaldehyde, the racemate of the female-produced sex pheromone on the pineapple mealy bug (*Dysmicoccus brevipes*) and its syn-isomer, tetrahedron, 72(4), pp. 6578-6588 (Year: 2016).*
Johnson, William S., et al., "A Simple Stereoselective Version of the Claisen Rearrangement Leading to trans-Trisubstituted Olefinic Bonds. Synthesis of Squalene", Journal of the American Chemical Society, 92(3), 1970, 741-742.
Mori, Kenji, "Pheromone synthesis. Part 260: Synthesis of (±)-(anti-1,2-dimethyl-3-methylenecyclopentyl) acetaldehyde, the racemate of the female-produced sex pheromone of the pineapple mealybug (*Dysmicoccus brevipes*), and its syn-isomer", Tetrahedron, 72(41), 2016, 6578-6588.

(Continued)

Primary Examiner — Yate' K Cutliff
(74) Attorney, Agent, or Firm — Myers Bigel, P.A.

(57) ABSTRACT

The present invention provides a process for preparing a (1,2-dimethyl-3-methylenecyclopentyl)acetate compound of the following general formula (3), wherein R represents a linear or branched alkyl group having 1 to 4 carbon atoms, the process comprising subjecting a haloacetaldehyde alkyl 2,3-dimethyl-2-cyclopentenyl acetal compound of the following general formula (1), wherein R is as defined above, and Y represents a halogen atom, to a dehydrohalogenation reaction in the presence of a base, followed by a rearrangement reaction to obtain a (1,2-dimethyl-2-cyclopentenyl) acetate compound of the following general formula (2), wherein R is as defined above, and subjecting the (1,2-dimethyl-2-cyclopentenyl)acetate compound (2) to an epoxidation reaction, followed by an isomerization reaction and then a methylenation reaction to obtain the (1,2-dimethyl-3-methylenecyclopentyl)acetate compound of the following general formula (3). The present invention also provides a process for preparing (1,2-dimethyl-3-methylenecyclopentyl)acetaldehyde of the following formula (4), the process comprising the aforesaid process for preparing the (1,2-dimethyl-3-methylenecyclopentyl)acetate compound (3), and converting an alkoxycarbonylmethyl group (i.e., —CH₂C(═O)OR) of the (1,2-dimethyl-3-methylenecyclopentyl)acetate compound (3) to a formylmethyl group (i.e., —CH₂CHO) to obtain (1,2-dimethyl-3-methylenecyclopentyl)acetaldehyde (4).

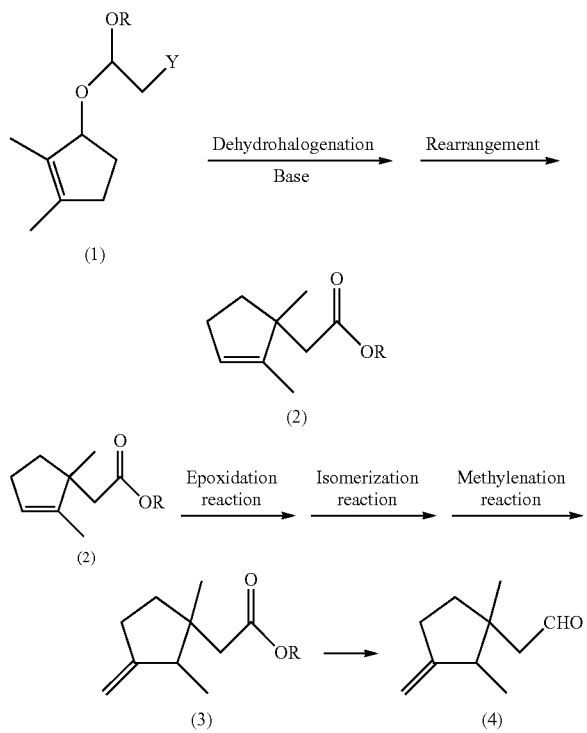

2 Claims, No Drawings

(56) References Cited

PUBLICATIONS

Mori, Kenji, "Pheromone synthesis. Part 262: Determination of the absolute configuration of the female sex pheromone [(1S,2S)-(-)-(1,2-dimethyl-3-methylenecyclopentyl) acetaldehyde] of the pineapple mealybug (*Dysmicoccus brevipes*) by synthesis coupled with X-ray analysi", Tetrahedron, 73(46), 2017, 6530-6541.

Tabata, Jun , et al., "Sex pheromone of a coccoid insect with sexual and asexual lineages: fate of an ancestrally essential sexual signal in parthenogenetic females", Journal of The Royal Society Interface, 14(128), 2017, 1-11.

Ramesh et al. "Enantiospecific Synthesis of Both Enantiomers of the Longtailed Mealybug Pheromone and Their Evaluation in a New Zealand Vineyard" The Journal of Organic Chemistry, 80:7785-7789 (2015).

Ramesh et al. "Syntheses and Determination of Absolute Configurations and Biological Activities of the Enantiomers of the Longtailed Mealybug Pheromone" Journal of Organic Chemistry, 78(12):6281-6284 (2013).

Zou et al. "Improved Synthesis of the Pheromone of the Longtailed Mealybug" Synlett, 15:2319-2321 (2010).

Extended European Search Report corresponding to European Patent Application No. 22177606.5 (5 pages) (dated Nov. 9, 2022).

Ainai et al. "Efficient Total Synthesis of 12-oxo-PDA and OPC-8:0" The Journal of Organic Chemistry, 68:7825-7832 (2003).

Curran et al. "Regiocontrol in opening of 2H-cyclopenta[b]furanones with organocopper reagents" The Journal of Organic Chemistry, 51:1614-1615 (1986).

Kobayashi et al. "Synthesis of Δ2-OPC-8:0 and OPC-6:0" Synlett, 14:2582-2584 (2004).

Rowlands et al. "The Use of Alkyl Vinyl Ethers in Olefin Synthesis" The Journal of Organic Chemistry, 17:807-811 (1952).

STN Registry No. 87453-51-8 (1 page) (entered STN Nov. 16, 1984) (Year: 1984).

Stork et al. "Free-Radical Cyclization of Bromoacetals. Use in the Construction of Bicyclic Acetals and Lactones" Journal of the American Chemical Society, 105:3741-3742 (1983).

Stork et al. "Regiospecific Trapping of Radicals from Cyclization Reactions. Cyclic Nitriles via Isocyanide Trapping" Journal of the American Chemical Society, 105:6765-6766 (1983).

Stork et al. "Vinyl Radical Cyclization. 2. Dicyclization via Selective Formation of Unsaturated Vinyl Radicals by Intramolecular Addition to Triple Bonds. Applications to the Synthesis of Butenolides and Furans" J Am Chem Soc, 105:3720-3722 (1983).

\* cited by examiner

PROCESSES FOR PREPARING A (1,2-DIMETHYL-3-METHYLENECYCLOPENTYL) ACETATE COMPOUND AND (1,2-DIMETHYL-3-METHYLENECYCLOPENTYL) ACETALDEHYDE

TECHNICAL FIELD

The present invention relates to a processes for preparing a (1,2-dimethyl-3-methylenecyclopentyl)acetate compound. The present invention also relates to a process for preparing (1,2-dimethyl-3-methylenecyclopentyl)acetaldehyde.

BACKGROUND ART

Pineapple mealybug (scientific name: *Dysmicoccus brevipes*) is a pest belonging to the order Hemiptera, and sucks the juice of many agricultural plants, such as pineapples, bananas, coffee, and citrus to damage these agricultural plants. Further, pineapple mealybugs discharge honeydew which contains sugar to cause fungi-induced diseases. These damage and diseases reduce the yield and quality of such agricultural plants, which is a serious problem.

Generally, insecticides have been used for controlling mealybugs. However, mealybugs live in narrow spaces behind leaves and/or plant barks and are themselves covered with a waxy substance. Therefore, insecticides are difficult to come in contact with the pest body. This results in insufficient effects of the insecticides.

In the light of adverse effects of insecticides on the environment and human health, there is recently a demand for the development of a new highly safe, and eco-friendly control method such as mating disruption and/or mass trapping using sex pheromones of insects. Development of such a new control method requires the industrial and inexpensive preparation of a sex pheromone in a large amount.

A sex pheromone of a sexually reproducing lineage of the pineapple mealybug is reported to be an optically active (1S,2S)-(−)-(1,2-dimethyl-3-methylenecyclopentyl)acetaldehyde (Non-Patent Literatures 1 and 2 listed below). It is reported that (1R,2R)-(+)-(1,2-dimethyl-3-methylenecyclopentyl)acetaldehyde which is an enantiomer, and (1R,2S)-(1,2-dimethyl-3-methylenecyclopentyl)acetaldehyde and (1S,2R)-(1,2-dimethyl-3-methylenecyclopentyl)acetaldehyde which are diastereomers of this sex pheromone do not adversely affect the attraction activity of natural sex pheromones (Non-Patent Literatures 1 and 2 listed below). Therefore, for the establishment of a technique for controlling the pests utilizing sex pheromones, it is thought to be efficient to establish a process for preparing these stereoisomer mixtures containing natural pheromones, in view of the inexpensive supply of the pheromone and for an economical control method.

One process for preparing a mixture of stereoisomers of this pheromone is reported as follows. 2,3-Dimethyl-2-cyclopenten-1-ol is acetylated, and then, the reaction product is reacted with a base, and subsequently, reacted with trimethylsilyl chloride, the reaction product is subjected to an Ireland-Claisen rearrangement reaction to form (1,2-dimethyl-2-cyclopentenyl)acetic acid as an intermediate, and then, the skeleton of the intermediate is transformed into the skeleton of the target compound, and the functional group of the transformed compound is converted into the target functional group of the target compound to form a mixture of the enantiomers and/or the diastereomers (Non-Patent Literatures 2 and 3 listed below)

Like the aforesaid Ireland-Claisen rearrangement reaction, a Johnson-Claisen rearrangement reaction is known as a Claisen rearrangement reaction of an allylalcohol such as a 2-cyclopenten-1-ol compound, in which the 2-cyclopenten-1-ol compound is reacted with a trialkyl orthoacetate in the presence of a weakly acidic catalyst such as propionic acid to form a (2-cyclopentenyl)acetate compound (Non-Patent Literature 4 listed below).

LIST OF THE LITERATURES

Non-Patent Literatures

[Non-Patent Literature 1] J. Tabata et al., J. R. Soc. Interface, 14, (2017). (downloadable from the following URL: <https://royalsocietypublishing.org/doi/10.1098/rsif.2017.0027>)
[Non-Patent Literature 2] K. Mori et al., Tetrahedron, 73 (2017)6530-6541.
[Non-Patent Literature 3] K. Mori et al., Tetrahedron, 72 (2016)6578-6588.
[Non-Patent Literature 4] W. S. Johnson et al., J. Am. Chem. Soc., 1970, 92, 741-743.

Problems to be Solved by the Invention

However, the preparation processes described in Non-Patent Literatures 2 and 3 using an Ireland-Claisen rearrangement reaction have such disadvantages that an organolithium compound and lithium amide, which are ignitable, are used; the reaction must be carried out at an extremely low temperature such as −78° C.; and industrially relatively expensive trialkylsilyl chloride is used.

In the process described in Non-Patent Literature 4 for preparing a (2-cyclopentenyl)acetate compound by a Johnson-Claisen rearrangement reaction in which a 2-cyclopenten-1-ol compound is reacted with a trialkyl orthoacetate in the presence of the weakly acidic catalyst, a dehydration reaction of the starting material, 2-cyclopenten-1-ol compound, occurs preferentially to cause a problematic low yield (see Comparative example 1 of the present specification). Thus, the prior art fails to industrially and economically prepare (1,2-dimethyl-2-cyclopentenyl)acetic acid and a (1,2-dimethyl-2-cyclopentenyl)acetate ester compound as the intermediate in a large amount.

SUMMARY OF THE INVENTION

The present invention has been made in these circumstances, and aims to overcome the aforesaid problems of the prior art and to provide an industrial and economical processes for preparing a (1,2-dimethyl-3-methylenecyclopentyl)acetate compound and (1,2-dimethyl-3-methylenecyclopentyl)acetaldehyde.

As a result of intensive research, the present inventors have now provided a haloacetaldehyde alkyl 2,3-dimethyl-2-cyclopentenyl acetal compound which is a novel compound, and have found that it is possible to prepare a (1,2-dimethyl-2-cyclopentenyl)acetate compound, without using an ignitable starting material and an industrially expensive starting material, in an industrially readily applicable range of a reaction temperature, by subjecting the haloacetaldehyde alkyl 2,3-dimethyl-2-cyclopentenyl acetal compound to a dehydrohalogenation reaction in the presence of a base, followed by a rearrangement reaction.

The present inventors have also found that it is possible to efficiently and industrially prepare a (1,2-dimethyl-3-methylenecyclopentyl)acetate compound by subjecting the (1,2-dimethyl-2-cyclopentenyl)acetate compound thus prepared to an epoxidation reaction, followed by an isomerization reaction, and then a methylenation reaction and, thus, have completed the present invention.

The present inventors have also found that it is possible to efficiently and industrially prepare (1,2-dimethyl-3-methylenecyclopentyl)acetaldehyde by converting an alkoxycarbonylmethyl group (i.e., —CH$_2$C(=O)OR) of the (1,2-dimethyl-3-methylenecyclopentyl)acetate compound thus prepared to a formylmethyl group (i.e., —CH$_2$CHO), and, thus, have completed the present invention.

According to one aspect of the present invention, the present invention provides a process for preparing a (1,2-dimethyl-3-methylenecyclopentyl)acetate compound of the following general formula (3):

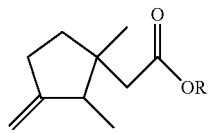

(3)

wherein R represents a linear or branched alkyl group having 1 to 4 carbon atoms, the process comprising:
subjecting a haloacetaldehyde alkyl 2,3-dimethyl-2-cyclopentenyl acetal compound of the following general formula (1):

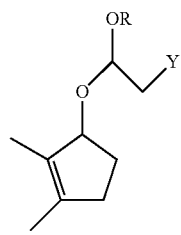

(1)

wherein R is as defined above, and Y represents a halogen atom,
to a dehydrohalogenation reaction in the presence of a base, followed by a rearrangement reaction to obtain a (1,2-dimethyl-2-cyclopentenyl)acetate compound of the following general formula (2):

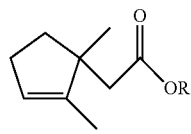

(2)

wherein R is as defined above, and
subjecting the (1,2-dimethyl-2-cyclopentenyl)acetate compound (2) to an epoxidation reaction, followed by an isomerization reaction, and then a methylenation reaction to obtain the (1,2-dimethyl-3-methylenecyclopentyl)acetate compound (3).

According to another aspect of the present invention, the present invention provides a process for preparing (1,2-dimethyl-3-methylenecyclopentyl)acetaldehyde (4) of the following general formula (4):

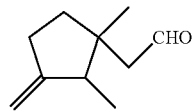

(4)

the process comprising:
the aforesaid process for preparing the (1,2-dimethyl-3-methylenecyclopentyl)acetate compound (3), and
converting an alkoxycarbonylmethyl group (i.e., —CH$_2$C(=O)OR) of the (1,2-dimethyl-3-methylenecyclopentyl)acetate compound (3) to a formylmethyl group (i.e., —CH$_2$CHO) to obtain (1,2-dimethyl-3-methylenecyclopentyl)acetaldehyde (4).

According to the present invention, the (1,2-dimethyl-2-cyclopentenyl)acetate compound (2) may be prepared without an ignitable starting material and an industrially expensive starting material, in an industrially readily applicable range of a reaction temperature. The (1,2-dimethyl-3-methylenecyclopentyl)acetate compound (3) may be prepared using the obtained (1,2-dimethyl-2-cyclopentenyl)acetate compound (2) as a synthetic intermediate and subjecting to an epoxidation reaction, followed by an isomerization reaction and then a methylenation reaction. (1,2-Dimethyl-3-methylenecyclopentyl)acetaldehyde (4) may be industrially and economically prepared by converting an alkoxycarbonylmethyl group (i.e., —CH$_2$C(=O)OR) of the obtained (1,2-dimethyl-3-methylenecyclopentyl)acetate compound (3) to a formylmethyl group (i.e., —CH$_2$CHO).

DETAILED DESCRIPTION OF PREFERRED EMBODIMENTS

Embodiments of the present invention will be described in detail below. It should be noted that the present invention is not limited to or by the embodiments.

A. Haloacetaldehyde alkyl 2,3-dimethyl-2-cyclopentenyl acetal compound which is a novel compound and of the following general formula (1) will be described in detail below.

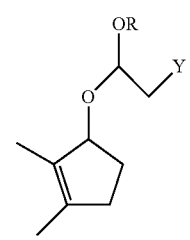

(1)

In the general formula (1), R represents a linear or branched alkyl group having 1 to 4 carbon atoms, and Y represents a halogen atom.

Examples of the alkyl group include linear alkyl groups such as a methyl group, an ethyl group, an n-propyl group, and an n-butyl group; and branched alkyl groups such as an isopropyl group and an isobutyl group. A methyl group, an ethyl group, and an n-propyl group are preferred in view of the reactivity and/or the yield.

Examples of the halogen atom include a chlorine atom, a bromine atom, and an iodine atom. A bromine atom or an iodine atom are preferred in view of the reactivity and/or the yield.

Examples of the haloacetaldehyde alkyl 2,3-dimethyl-2-cyclopentenyl acetal compound (1) include the following compounds:

chloroacetaldehyde linear alkyl 2,3-dimethyl-2-cyclopentenyl acetal compounds such as chloroacetaldehyde 2,3-dimethyl-2-cyclopentenyl methyl acetal, chloroacetaldehyde 2,3-dimethyl-2-cyclopentenyl ethyl acetal, chloroacetaldehyde 2,3-dimethyl-2-cyclopentenyl n-propyl acetal, and chloroacetaldehyde n-butyl 2,3-dimethyl-2-cyclopentenyl acetal;

bromoacetaldehyde linear alkyl 2,3-dimethyl-2-cyclopentenyl acetal compounds such as bromoacetaldehyde 2,3-dimethyl-2-cyclopentenyl methyl acetal, bromoacetaldehyde 2,3-dimethyl-2-cyclopentenyl ethyl acetal, bromoacetaldehyde 2,3-dimethyl-2-cyclopentenyl n-propyl acetal, and bromoacetaldehyde n-butyl 2,3-dimethyl-2-cyclopentenyl acetal;

iodoacetaldehyde linear alkyl 2,3-dimethyl-2-cyclopentenyl acetal compounds such as iodoacetaldehyde 2,3-dimethyl-2-cyclopentenyl methyl acetal, iodoacetaldehyde 2,3-dimethyl-2-cyclopentenyl ethyl acetal, iodoacetaldehyde 2,3-dimethyl-2-cyclopentenyl n-propyl acetal, and iodoacetaldehyde n-butyl 2,3-dimethyl-2-cyclopentenyl acetal;

chloroacetaldehyde branched alkyl 2,3-dimethyl-2-cyclopentenyl acetal compounds such as chloroacetaldehyde 2,3-dimethyl-2-cyclopentenyl isopropyl acetal, and chloroacetaldehyde 2,3-dimethyl-2-cyclopentenyl isobutyl acetal;

bromoacetaldehyde branched alkyl 2,3-dimethyl-2-cyclopentenyl acetal compounds such as bromoacetaldehyde 2,3-dimethyl-2-cyclopentenyl isopropyl acetal, and bromoacetaldehyde 2,3-dimethyl-2-cyclopentenyl isobutyl acetal; and iodoacetaldehyde branched alkyl 2,3-dimethyl-2-cyclopentenyl acetal compounds such as iodoacetaldehyde 2,3-dimethyl-2-cyclopentenyl isopropyl acetal, and iodoacetaldehyde 2,3-dimethyl-2-cyclopentenyl isobutyl acetal.

Specifically, the bromoacetaldehyde linear alkyl 2,3-dimethyl-2-cyclopentenyl acetal compound and the iodoacetaldehyde linear alkyl 2,3-dimethyl-2-cyclopentenyl acetal compound are preferred as the haloacetaldehyde alkyl 2,3-dimethyl-2-cyclopentenyl acetal compound (1) in view of the reactivity.

Furthermore, the haloacetaldehyde alkyl 2,3-dimethyl-2-cyclopentenyl acetal compound (1) may be its enantiomers, diastereomers, and a mixture of such stereoisomers in the same or different amounts.

Next, a process for preparing the haloacetaldehyde alkyl 2,3-dimethyl-2-cyclopentenyl acetal compound (1) will be described below.

The haloacetaldehyde alkyl 2,3-dimethyl-2-cyclopentenyl acetal compound (1) may be prepared, for example by halogenating an alkyl vinyl ether compound of the following general formula (9) with a halogenating agent to form a halide and, subsequently, subjecting the obtained halide to a substitution reaction with 2,3-dimethyl-2-cyclopenten-1-ol of the following formula (10), as shown in the following reaction formula (see, for example, the following Synthesis Example 1).

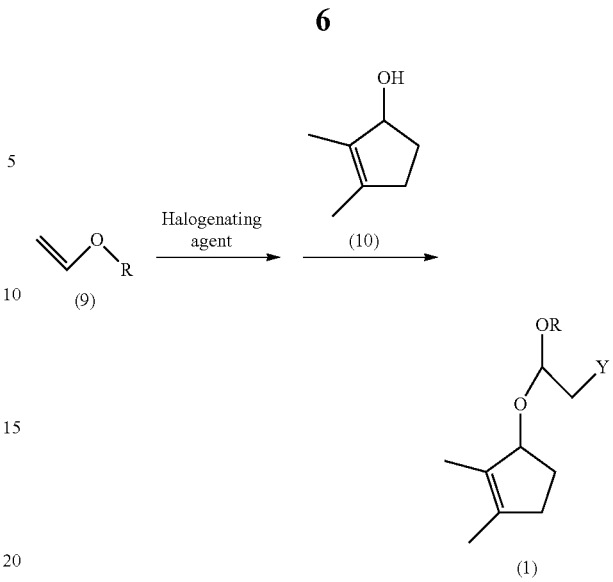

The process for preparing the haloacetaldehyde alkyl 2,3-dimethyl-2-cyclopentenyl acetal compound (1) will be further described in detail below.

The alkyl vinyl ether compound (9) which is the starting material, will be described below.

R in the general formula (9) is as defined for the general formula (1).

Examples of the alkyl vinyl ether compound (9) include linear alkyl vinyl ethers such as methyl vinyl ether, ethyl vinyl ether, n-propyl vinyl ether, and n-butyl vinyl ether; and branched alkyl vinyl ethers such as isopropyl vinyl ethers and isobutyl vinyl ethers.

The alkyl vinyl ether compound (9) may be commercially available one or may be prepared in house.

The halogenation of the alkyl vinyl ether compound (9) may be carried out with a halogenating agent and may be carried out with heating or cooling, if needed.

Examples of the halogenating agent used in the halogenation include chlorinating agents such as chlorine, sulfuryl chloride, N-chlorosuccinimide, iodobenzene dicholoride, tetrabutylammonium iodotetrachloride, titanium (IV) chloride, and copper (II) chloride; brominating agents such as bromine, N-bromosuccinimide, N-bromoacetamide, 1,3-dibromo-5,5-dimethylhydantoin, tetrabutylammonium tribromide, phenyltrimethylammonium tribromide, iodobenzene dibromide, copper (II) bromide, copper (I) bromide, magnesium (II) bromide, and aluminum bromide; iodinating agents such as iodine, N-iodosuccinimide, and 1,3-diiodo-5,5-dimethylhydantoin; and chloro-iodinating agents such as iodine monochloride and potassium tetrachloroiodate. The brominating agent and the iodinating agent are preferred. Bromine and N-bromosuccinimide among the brominating agent, and iodine and N-iodosuccinimide among the iodinating agents are more preferred in view of the reactivity and/or the yield.

An amount of the halogenating agent used in the halogenation varies, depending on the structure and/or the reactivity of the alkyl vinyl ether compound (9) and/or the halogenating agent, and is preferably from 0.2 mol to 5.0 mol, more preferably from 0.5 mol to 2.0 mol, per mol of the alkyl vinyl ether compound (9) in view of the yield and/or the by-production of an impurity.

A solvent used in the halogenation may be any solvent that has no adverse effect on the halogenation. Examples of the solvent used in the halogenation include halogen-based solvents such as methylene chloride, chloroform, carbon tetrachloride, and 1,2-dichloroethane; ether solvents such as diethyl ether, di-n-butyl ether, di-t-butyl ether, tetrahydrofuran, 1,4-dioxane, and diethyleneglycol dimethyl ether; hydrocarbon solvents such as hexane and heptane; and aprotic polar solvents such as N,N-dimethylformamide, N,N-dimethylacetamide, dimethyl sulfoxide, and hexamethylphosphoric triamide. Halogen-based solvents, ether solvents, and aprotic polar solvents are preferred in view of the reactivity.

The solvent may be used either alone or in combination thereof, if necessary, and may be optionally determined while considering the type and/or the reactivity and/or the selectivity of the alkyl vinyl ether compound (9) and/or the halogenating agent.

An amount of the solvent used in the halogenation may be optionally determined while considering the type and/or the reactivity of the alkyl vinyl ether compound (9) and/or the halogenating agent and is, for example, preferably from 50 g to 10,000 g, more preferably from 500 g to 8,000 g, per mol of the alkyl vinyl ether compound (9) in view of the reactivity and/or the by-production of an impurity.

A reaction temperature of the halogenation may be optionally determined while considering the reactivity of the alkyl vinyl ether compound (9) and/or the halogenating agent and/or the by-production of an impurity and is, for example, preferably from −60° C. to 150° C., more preferably from −20° C. to 50° C., in view of the reactivity and/or the by-production of an impurity.

The reaction time of the halogenation is preferably optimized, depending on the reactivity of the alkyl vinyl ether compound (9) and/or the halogenating agent by monitoring the reaction progress with, for example, gas chromatography and/or thin layer chromatography to confirm the disappearance of the alkyl vinyl ether compound (9) and/or the halogenating agent. For example, the reaction time of the halogenation is preferably from 0.5 hours to 168 hours, more preferably from 0.5 hours to 24 hours, even more preferably from 0.5 hours to 6 hours, in view of the yield and/or the formation of an impurity.

A halide obtained from the halogenation of the alkyl vinyl ether compound (9) with the halogenating agent is thought to be an alkyl 1,2-dihaloethyl ether of the following general formula (11). The halide may be isolated and/or purified after the halogenation, and then used in a subsequent step or may be used as such in the reaction mixture in a subsequent step without isolation and/or purification after the halogenation.

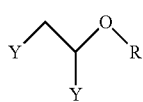

(11)

In the general formula (11), R is as defined for the general formula (9), and Y represent, independently of each other, a halogen atom. Examples of the halogen atom include a chlorine atom, a bromine atom, and an iodine atom. A bromine atom or an iodine atom is preferred in view of the yield and/or the reactivity. Y may be, independently of each other, the same or different. When the halogenating agent is, for example, a chloro-iodinating agent such as iodine monochloride or potassium tetrachloroiodate, Y may be, independently of each other, different.

Next, 2,3-dimethyl-2-cyclopenten-1-ol (10) may be commercially available one or may be prepared in house.

In the substitution reaction, the halogen atom (i.e., the secondary Y) in the halide is substituted with 2,3-dimethyl-2-cyclopenten-1-ol (10) to form the haloacetaldehyde alkyl 2,3-dimethyl-2-cyclopentenyl acetal compound (1).

An amount of 2,3-dimethyl-2-cyclopenten-1-ol (10) used is preferably from 0.2 mol to 5.0 mol, more preferably from 0.5 mol to 2.0 mol, per mol of the alkyl vinyl ether compound (9) in view of the yield and/or the formation of a by-product and/or the economy.

The substitution reaction may be carried out with heating or cooling, if needed. The substitution reaction may be carried out in the presence of a base while considering the reactivity of 2,3-dimethyl-2-cyclopenten-1-ol (10) and/or the halide and/or the by-production of an impurity.

Examples of the base include amines such as triethylamine, diisopropylethylamine, pyridine, N,N-dimethylaminopyridine, and N,N-dimethylaniline; organometallic compounds such as n-butyl lithium, methyl lithium, and phenyl lithium; metal amides such as lithium diisopropylamide, lithium hexamethyldisilazide, sodium hexamethyldisilazide, and lithium dicyclohexylamide; metal hydroxides such as sodium hydroxide and potassium hydroxide; and metal carbonates such as potassium carbonate, sodium carbonate, and sodium bicarbonate.

The base may be used either alone or in combination thereof, if necessary, and may be optionally determined while considering the reactivity of 2,3-dimethyl-2-cyclopenten-1-ol (10) and/or the halide and/or the formation of an impurity.

An amount of the base may be optionally determined while considering the reactivity of 2,3-dimethyl-2-cyclopenten-1-ol (10) and/or the halide and/or the formation of an impurity, and is, for example, preferably from 0.5 mol to 5.0 mol, more preferably from 0.8 mol to 2.0 mol, per mol of 2,3-dimethyl-2-cyclopenten-1-ol (10), in view of the reactivity and/or the economy.

A solvent used in the substitution reaction may be any solvent that has no adverse effect on the substitution reaction. Examples of the solvent used in the substitution reaction include halogen-based solvents such as methylene chloride, chloroform, carbon tetrachloride, and 1,2-dichloroethane; hydrocarbon solvents such as hexane, heptane, benzene, and toluene; ether solvents such as diethyl ether, tetrahydrofuran, 1,4-dioxane, and diethylene glycol dimethyl ether; nitrile solvents such as acetonitrile; ketone solvents such as acetone, methyl ethyl ketone, and diisobutyl ketone; ester solvents such as ethyl acetate and butyl acetate; and aprotic polar solvents such as N,N-dimethylformamide, N,N-dimethylacetamide, dimethyl sulfoxide, and hexamethylphosphoric triamide. The halogen-based solvents, the ether solvents, and the aprotic polar solvents are preferred in view of the reactivity and/or the yield The solvent may be used either alone or in combination thereof, if necessary, and may be optionally determined while considering the type and/or the reactivity and/or the selectivity of 2,3-dimethyl-2-cyclopenten-1-ol (10) and/or the halide.

A solvent used in the substitution reaction may be the solvent already used in the halogenation as such. The same species of solvent as in the halogenation or any solvent different from the solvent used in the halogenation may be added into the substitution reaction system to increase the reactivity and/or adjust the concentration.

An amount of the solvent used in the substitution reaction may be optionally determined while considering the reactivity of 2,3-dimethyl-2-cyclopenten-1-ol (10) and/or the halide and/or the formation of an impurity, and is for example, preferably from 50 g to 10,000 g, more preferably from 500 g to 8,000 g, per mol of 2,3-dimethyl-2-cyclopenten-1-ol (10) in view of the reactivity and/or the by-production of an impurity.

A reaction temperature of the substitution reaction may be optionally determined while considering the reactivity of 2,3-dimethyl-2-cyclopenten-1-ol (10) and/or the halide and/or the formation of an impurity and is, for example, preferably from −60° C. to 150° C., more preferably from −20° C. to 50° C., in view of the reactivity and/or the formation of an impurity.

The reaction time of the substitution reaction is preferably optimized, depending on the reactivity of 2,3-dimethyl-2-cyclopenten-1-ol (10) and/or the halide, by monitoring the reaction progress with, for example, gas chromatography and/or thin layer chromatography to confirm the disappearance of 2,3-dimethyl-2-cyclopenten-1-ol (10) and/or the halide. For example, the reaction time of the substitution reaction is preferably from 1 hour to 168 hours, more preferably from 1 hour to 24 hours, even more preferably from 1 hour to 6 hours, in view of the yield and/or the formation of an impurity.

The haloacetaldehyde alkyl 2,3-dimethyl-2-cyclopentenyl acetal compound (1) formed in the substitution reaction may be suitably isolated and/or purified in any purification method used in usual organic synthesis such as distillation at a reduced pressure and/or various chromatography. Distillation at a reduced pressure is preferred in view of the industrial economy. When the haloacetaldehyde alkyl 2,3-dimethyl-2-cyclopentenyl acetal compound (1) formed in the substitution reaction has a sufficient purity, the crude product comprising the haloacetaldehyde alkyl 2,3-dimethyl-2-cyclopentenyl acetal compound (1) may be used as such without purification in a subsequent step.

B. Next, the process for preparing the (1,2-dimethyl-2-cyclopentenyl)acetate compound of the following general formula (2) will be described below.

The (1,2-dimethyl-2-cyclopentenyl)acetate compound (2) may be prepared by subjecting the haloacetaldehyde alkyl 2,3-dimethyl-2-cyclopentenyl acetal compound (1) to a dehydrohalogenation (−HY) reaction in the presence of a base, followed by a rearrangement reaction, as shown in the following reaction formula (see Example 1-1 below).

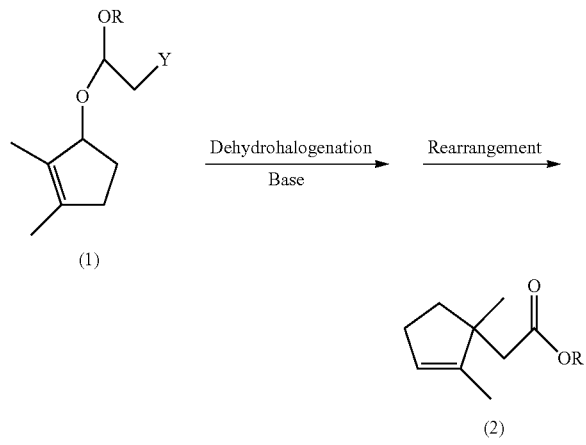

The haloacetaldehyde alkyl 2,3-dimethyl-2-cyclopentenyl acetal compound (1), which is the starting material, is as mentioned above.

Next, the (1,2-dimethyl-2-cyclopentenyl)acetate compound (2) to be formed in the rearrangement reaction will be described below.

R in the general formula (2) is as defined for the general formula (1).

Examples of the (1,2-dimethyl-2-cyclopentenyl)acetate compound (2) include linear alkyl (1,2-dimethyl-2-cyclopentenyl)acetates such as methyl (1,2-dimethyl-2-cyclopentenyl)acetate, ethyl (1,2-dimethyl-2-cyclopentenyl)acetate, n-propyl (1,2-dimethyl-2-cyclopentenyl)acetate, and n-butyl (1,2-dimethyl-2-cyclopentenyl)acetate; and branched alkyl (1,2-dimethyl-2-cyclopentenyl)acetate such as isopropyl (1,2-dimethyl-2-cyclopentenyl)acetate, and isobutyl (1,2-dimethyl-2-cyclopentenyl)acetate.

Furthermore, when R in the general formula (2) does not have any asymmetric carbon atom, the (1,2-dimethyl-2-cyclopentenyl)acetate compound (2) includes an (R)-(1,2-dimethyl-2-cyclopentenyl)acetate compound, an (S)-(1,2-dimethyl-2-cyclopentenyl)acetate compound, and the racemic and scalemic mixtures thereof. On the other hand, when R in the general formula (2) has one or more asymmetric carbon atoms, the (1,2-dimethyl-2-cyclopentenyl) acetate compound (2) may be its enantiomers, diastereomers, and a mixture of such stereoisomers in the same or different amounts.

The dehydrohalogenation reaction may be carried out in the presence of a base, and may be carried out with heating or cooling, if needed.

Examples of the base used in the dehydrohalogenation reaction include metal alkoxides such as sodium methoxide, sodium ethoxide, sodium t-butoxide, lithium methoxide, lithium ethoxide, lithium t-butoxide, potassium methoxide, potassium ethoxide, and potassium t-butoxide; metal hydroxides such as sodium hydroxide, lithium hydroxide, and potassium hydroxide; organometallic reagents such as methyl lithium, ethyl lithium, n-butyl lithium and methylmagnesium chloride; metal amides such as lithium diisopropylamide, lithium hexamethyldisilazide, sodium hexamethyldisilazide, and lithium dicyclohexylamide; and organic nitrogen compounds such as triethylamine, diisopropylethylamine, tributylamine, N,N-dimethylaniline, pyridine, 4-dimethylaminopyridine, pyrrolidine, piperidine, collidine, lutidine, morpholine, piperazine, azabicyclo[5.4.0]undeca-7-ene, and 1,5-diazabicyclo[4.3.0]nona-5-ene. Metal alkoxides are preferred in view of the reactivity and/or the formation of an impurity.

The base may be used either alone or in combination thereof, if necessary, and may be optionally determined while considering the type and/or the reactivity and/or the selectivity of haloacetaldehyde alkyl 2,3-dimethyl-2-cyclopentenyl acetal compound (1).

An amount of the base varies, depending on the structure and/or the reactivity of the haloacetaldehyde alkyl 2,3-dimethyl-2-cyclopentenyl acetal compound (1). For example, the amount is preferably from 0.2 mol to 5.0 mol per mol of the haloacetaldehyde alkyl 2,3-dimethyl-2-cyclopentenyl acetal compound (1), more preferably from 0.5 mol to 2.0 mol, in view of the yield and/or the formation of an impurity.

A solvent used in the dehydrohalogenation reaction may be any solvent that has no adverse effect on the dehydrohalogenation reaction. Examples of the solvent used in the dehydrohalogenation reaction include alcoholic solvents such as methanol, ethanol, isopropyl alcohol, and t-butyl alcohol; ether solvents such as diethyl ether, di-n-butyl ether, di-t-butyl ether, tetrahydrofuran, 1,4-dioxane, diethyleneglycol dimethyl ether, and diethyleneglycol diethyl ether; hydrocarbon solvents such as hexane, heptane, benzene, toluene, and xylene; aprotic polar solvents such as N, N-dimethylformamide, N, N-dimethylacetamide, 1,3-dimethyl-2-imidazolidinone, dimethyl sulfoxide, and hexamethylphosphoric triamide; and nitrile solvents such as acetonitrile. The ether solvents and the aprotic polar solvents are preferred in view of the reactivity, and N,N-dimethylformamide, N,N-dimethylacetamide, diethyleneglycol dimethyl ether, and diethyleneglycol diethyl ether are more preferred in view of the reactivity.

The solvent may be used either alone or in combination thereof, if necessary, and may be optionally determined while considering the type and/or the reactivity and/or the selectivity of the haloacetaldehyde alkyl 2,3-dimethyl-2-cyclopentenyl acetal compound (1).

An amount of the solvent may be optionally determined while considering the reactivity and/or the solubility of the haloacetaldehyde alkyl 2,3-dimethyl-2-cyclopentenyl acetal compound (1) and is, for example, preferably from 30 g to 10,000 g, more preferably and 100 g to 5,000 g, per mol of the haloacetaldehyde alkyl 2,3-dimethyl-2-cyclopentenyl acetal compound (1) in view of the reactivity and/or the economy.

A reaction temperature of the dehydrohalogenation reaction may be optionally determined while considering the reactivity of the haloacetaldehyde alkyl 2,3-dimethyl-2-cyclopentenyl acetal compound (1) and/or the formation of an impurity and is, for example, preferably from −60° C. to 150° C., more preferably from −20° C. to 80° C., in view of the reactivity and/or the formation of an impurity.

The reaction time of the dehydrohalogenation reaction is preferably optimized, depending on the reactivity of the haloacetaldehyde alkyl 2,3-dimethyl-2-cyclopentenyl acetal compound (1), by monitoring the reaction progress with, for example, gas chromatography and/or thin layer chromatography to confirm the disappearance of the haloacetaldehyde alkyl 2,3-dimethyl-2-cyclopentenyl acetal compound (1) which is a substrate. For example, the reaction time of the dehydrohalogenation reaction is preferably from 1 hour to 168 hours, more preferably from 1 hour to 24 hours, even more preferably from 1 hour to 12 hours, in view of the yield and/or the formation of an impurity.

During the dehydrohalogenation reaction, an alkyl 2,3-dimethyl-2-cyclopentenyl ketene acetal compound of the following general formula (5) is thought to be formed in the reaction system as a product of the dehydrohalogenation reaction.

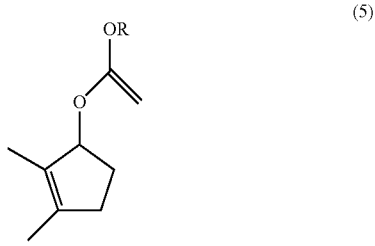

(5)

R in the general formula (5) is as defined for the general formula (1).

The product of the dehydrohalogenation reaction may be isolated and/or purified in any purification method used in usual organic synthesis such as distillation at a reduced pressure and/or various chromatography, and then may be used in a subsequent rearrangement reaction. When the product of the dehydrohalogenation reaction is difficult to be isolated and/or purified due to its nature, the product is preferably used as is in a subsequent rearrangement reaction.

Next, in the rearrangement reaction, a (1,2-dimethyl-2-cyclopentenyl)acetate compound (2) is prepared from the product of the dehydrohalogenation reaction via a [3,3]-sigmatropic rearrangement as shown in the following reaction formula. The carbon atom attached to the alkoxycarbonylmethyl group becomes quaternary, resulting in greater steric hindrance of the (1,2-dimethyl-2-cyclopentenyl)acetate compound (2) and difficulty in preparation of the (1,2-dimethyl-2-cyclopentenyl)acetate compound (2) using usual anion species. Therefore, the preparation method utilizing the [3,3]-sigmatropic rearrangement is thought to be effective in the process for preparing the (1,2-dimethyl-2-cyclopentenyl)acetate compound (2).

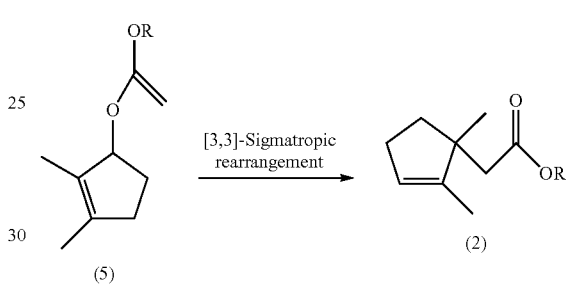

The rearrangement reaction may be carried out in a solvent or without a solvent, and may be carried out with heating or cooling, if needed.

A solvent used in the rearrangement reaction may be any solvent that has no adverse effect on the rearrangement reaction. Examples of the solvent used in the rearrangement reaction include alcoholic solvents such as methanol, ethanol, isopropyl alcohol, and t-butyl alcohol; ether solvents such as diethyl ether, di-n-butyl ether, di-t-butyl ether, tetrahydrofuran, 1,4-dioxane, and diethyleneglycol dimethyl ether; hydrocarbon solvents such as hexane, heptane, benzene, toluene, and xylene; aprotic polar solvents such as N,N-dimethylformamide, N,N-dimethylacetamide, 1,3-dimethyl-2-imidazolidinone, dimethyl sulfoxide, and hexamethylphosphoric triamide; and nitrile solvents such as acetonitrile. The ether solvents and the aprotic polar solvents are preferred in view of the reactivity.

The solvent may be used either alone or in combination thereof, if necessary, and may be optionally determined while considering the type and/or the reactivity of the product of the dehydrohalogenation reaction When the product of the dehydrohalogenation reaction is used in a subsequent rearrangement reaction without being isolated and/or purified, a solvent to be used in the rearrangement reaction may be the solvent itself used in the dehydrohalogenation reaction. Any solvent may be additionally used in the rearrangement reaction system to adjust the reaction temperature and/or concentration.

An amount of the solvent used in the rearrangement reaction may be optionally determined while considering the reactivity and/or the solubility of the product of the dehydrohalogenation reaction which is the substrate for the rearrangement reaction. For example, an amount of the solvent used is preferably more than 0 g to 10,000 g, more preferably from 50 g to 3,000 g, per mol of the haloacetaldehyde alkyl 2,3-dimethyl-2-cyclopentenyl acetal compound (1) or the product of the dehydrohalogenation reaction in view of the reactivity and/or the economy.

A reaction temperature of the rearrangement reaction may be optionally determined while considering the reactivity of the product of the dehydrohalogenation reaction and/or the formation of an impurity and is, for example, preferably from −60° C. to 250° C., more preferably from 0° C. to 150° C., even more preferably from 80° C. to 120° C., in view of the reactivity and/or the formation of an impurity.

The reaction time of the rearrangement reaction is preferably optimized, depending on the reactivity of the product of the dehydrohalogenation reaction, by monitoring the reaction progress with, for example, gas chromatography and/or thin layer chromatography to confirm the disappearance of the product of the dehydrohalogenation reaction. For example, the reaction time of the rearrangement reaction is preferably from 1 hour to 168 hours, more preferably from 1 hour to 24 hours, even more preferably from 1 hour to 6 hours, in view of the yield and/or the formation of an impurity.

The (1,2-dimethyl-2-cyclopentenyl)acetate compound (2) formed in the rearrangement reaction may be suitably isolated and/or purified in any purification method used in usual organic synthesis such as distillation at a reduced pressure and/or various chromatography. Distillation at a reduced pressure is preferred in view of the industrial economy. When the (1,2-dimethyl-2-cyclopentenyl)acetate compound (2) formed in the rearrangement reaction has a sufficient purity, the crude product comprising (1,2-dimethyl-2-cyclopentenyl)acetate compound (2) may be used as such without purification in a subsequent step.

C. The process for preparing the (1,2-dimethyl-3-methylenecyclopentyl)acetate compound of the following formula (3) will be described below.

The (1,2-dimethyl-3-methylenecyclopentyl)acetate compound (3) may be obtained by subjecting the (1,2-dimethyl-2-cyclopentenyl)acetate compound (2) obtained in B to an epoxidation reaction, followed by an isomerization reaction, and then a methylenation reaction, as shown in the following reaction formula (see Example 2-1 to Example 2-3 below).

In detail, the (1,2-dimethyl-3-methylenecyclopentyl)acetate compound (3) may be prepared by subjecting a (1,2-dimethyl-2-cyclopentenyl)acetate compound (2) to an epoxidation reaction to obtain the (1,2-dimethyl-2,3-epoxycyclopentyl)acetate compound of the following formula (6), subjecting the obtained (1,2-dimethyl-2,3-epoxycyclopentyl)acetate compound (6) to an isomerization reaction to obtain the (1,2-dimethyl-3-oxocyclopentyl)acetate compound of the following formula (7), followed by subjecting the obtained (1,2-dimethyl-3-oxocyclopentyl)acetate compound (7) to a methylenation reaction.

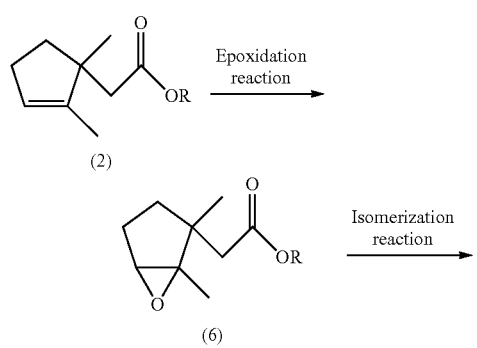

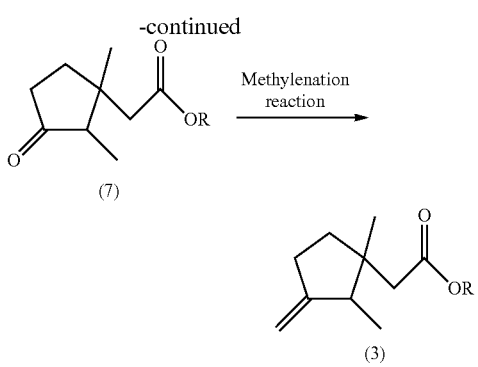

C-1. Epoxidation Reaction

The (1,2-dimethyl-2-cyclopentenyl)acetate compound (2), which is the starting material, will be described below.

The (1,2-dimethyl-2,3-epoxycyclopentyl)acetate compound (6) to be formed in the epoxidation reaction will be described below.

R in the general formula (6) is as defined for the general formula (1).

Examples of the (1,2-dimethyl-2,3-epoxycyclopentyl)acetate compound (6) include linear alkyl (1,2-dimethyl-2,3-epoxycyclopentenyl)acetates such as methyl (1,2-dimethyl-2,3-epoxycyclopentenyl)acetate, ethyl (1,2-dimethyl-2,3-epoxycyclopentenyl)acetate, n-propyl (1,2-dimethyl-2,3-epoxycyclopentenyl)acetate, and n-butyl (1,2-dimethyl-2,3-epoxycyclopentenyl)acetate; and branched alkyl (1,2-dimethyl-2,3-epoxycyclopentenyl)acetate such as isopropyl (1,2-dimethyl-2,3-epoxycyclopentenyl)acetate, and isobutyl (1,2-dimethyl-2,3-epoxycyclopentenyl)acetate.

Examples of the (1,2-dimethyl-2,3-epoxycyclopentyl)acetate compound (6) may be its enantiomers, diastereomers, and a mixture of such stereoisomers in the same or different amounts.

The aforementioned epoxidation may be carried out using an epoxidation reaction using a known epoxidizing agent, and may be carried out with heating or cooling, if needed.

Examples of the epoxidizing agent used in the epoxidation reaction include an organic percarboxylic acid compounds having from 1 to 7 carbon atoms such as performic acid, peracetic acid, perpropionic acid, pertrifluoroacetic acid, perbenzoic acid, m-chloroperoxybenzoic acid, and 4-nitroperbenzoic acid; and dioxirane compounds such as 3,3-dimethyl-1,2-dioxirane, 3-ethyl-3-methyl-1,2-dioxirane, 3-methyl-3-trifluoromethyl-1,2-dioxirane, 3,3-difluoro-1,2-dioxirane, and 1,2-dioxaspiro[2,5]octane. Among these epoxidizing agent, preferred is performic acid, peracetic acid or m-chloroperbenzoic acid, more preferred is m-chloroperbenzoic acid, in view of the reactivity, and/or the yield, and/or the handling ease.

The epoxidizing agent may be used either alone or in combination thereof, if necessary, and may be optionally determined while considering the type and/or the reactivity of the (1,2-dimethyl-2-cyclopentenyl)acetate compound (2).

The amount of epoxidizing agent is preferably from 1.0 mol to 5.0 mol, more preferably from 1.0 mol to 1.5 mol, per mol of the (1,2-dimethyl-2-cyclopentenyl)acetate compound (2) in view of the economy and/or the reactivity.

The epoxidation reaction may be carried out using asymmetric epoxidation under Jacobsen-Katsuki epoxidation conditions or Shi asymmetric epoxidation conditions.

When an organic percarboxylic acid compound is used as the epoxidizing agent, an alkali metal hydrogen carbonate such as sodium hydrogen carbonate may be added into the reaction system, if necessary, in view of prevention of the epoxidation reaction system from becoming acidic due to a carboxylic acid compound derived from the organic percarboxylic acid compound.

Examples of the solvent used in the epoxidation reaction include halogen-based solvents such as methylene chloride, chloroform, carbon tetrachloride, trichloroethane, and tetrachloroethane; hydrocarbon solvents such as pentane, hexane, heptane, and cyclohexane; aromatic solvents such as benzene and toluene; ether solvents such as diethyl ether, tetrahydrofuran, 1,4-dioxane, t-butyl methyl ether, and methyltetrahydropyran; ester solvents such as methyl acetate, ethyl acetate, and butyl acetate; and nitrile solvents such as acetonitrile. Dichloromethane, chloroform, tetrahydrofuran, or ethyl acetate is preferred in view of the reactivity and/or the yield.

The solvent may be used either alone or in combination thereof, if necessary, and may be optionally determined while considering the type and/or the reactivity of the (1,2-dimethyl-2-cyclopentenyl)acetate compound (2).

An amount of the solvent is preferably from 200 g to 10,000 g, more preferably from 1,000 g to 5,000 g, per mol of the (1,2-dimethyl-2-cyclopentenyl)acetate compound (2) in view of the economy and/or the reactivity.

A reaction temperature of the epoxidation reaction is, for example, preferably from −30° C. to 100° C., more preferably from −10° C. to 50° C., in view of the reaction rate and/or the yield.

The reaction time of the epoxidation reaction is preferably optimized, depending on the reactivity of the (1,2-dimethyl-2-cyclopentenyl)acetate compound (2), by monitoring the reaction progress with, for example, gas chromatography and/or thin layer chromatography to confirm the disappearance of the (1,2-dimethyl-2-cyclopentenyl)acetate compound (2), and is, for example, preferably from 1 hour to 168 hours, more preferably from 1 hour to 24 hours, even more preferably from 1 hour to 12 hours, in view of the yield and/or the formation of an impurity.

C-2. Isomerization Reaction

The (1,2-dimethyl-2,3-epoxycyclopentyl) acetate compound (6), which is the starting material, will be described below.

The (1,2-dimethyl-3-oxocyclopentyl)acetate compound (7) to be formed in the isomerization reaction will be described below.

R in the general formula (7) is as defined for the general formula (1).

Examples of the (1,2-dimethyl-3-oxocyclopentyl)acetate compound (7) include linear alkyl (1,2-dimethyl-3-oxocyclopentyl)acetates such as methyl (1,2-dimethyl-3-oxocyclopentyl)acetate, ethyl (1,2-dimethyl-3-oxocyclopentyl)acetate, n-propyl (1,2-dimethyl-3-oxocyclopentyl)acetate, and n-butyl (1,2-dimethyl-3-oxocyclopentyl)acetate; and branched alkyl (1,2-dimethyl-3-oxocyclopentyl)acetates such as isopropyl (1,2-dimethyl-3-oxocyclopentyl)acetate, and isobutyl (1,2-dimethyl-3-oxocyclopentyl)acetate.

Examples of the (1,2-dimethyl-3-oxocyclopentyl)acetate compound (7) to be formed in the isomerization reaction may be its enantiomers, diastereomers, and a mixture of such stereoisomers in the same or different amounts.

The isomerization may be carried out using a known isomerization reaction, for example, an isomerization reaction under acidic conditions in a presence of an acid or under basic conditions in a presence of a base, and may be carried out with heating or cooling, if needed.

Examples of the acid include inorganic acids such as sulfuric acid, phosphoric acid, and perchloric acid; organic acids such as methanesulfonic acid, benzenesulfonic acid, and p-toluenesulfonic acid; solid acids such as alumina, titania, zeolite, and Amberlyst 15; and Lewis acids such as zinc chloride (II), zinc bromide (II), aluminum chloride (III), and boron trifluoride complex.

The acid may be used either alone or in combination thereof, if necessary, and may be optionally determined while considering the type and/or the reactivity of the (1,2-dimethyl-2,3-epoxycyclopentyl)acetate compound (6).

Examples of the base include metal hydroxides such as lithium hydroxide and potassium hydroxide; organolithium reagents such as methyllithium, ethyllithium, and n-butyllithium; and lithium amides such as lithium diisopropylamide and lithium hexamethyldisilazide.

The base may be used either alone or in combination thereof, if necessary, and may be optionally determined while considering the type and/or the reactivity of the (1,2-dimethyl-2,3-epoxycyclopentyl)acetate compound (6).

The amount of acid and base used in the isomerization reaction differs due to the structure and/or the reactivity of the (1,2-dimethyl-2,3-epoxycyclopentyl)acetate compound (6), and is preferably from 0.01 mol to 2.0 mol, more preferably from 0.1 mol to 1.0 mol, per mol of the (1,2-dimethyl-2,3-epoxycyclopentyl)acetate compound (6) in view of the yield and/or the formation of an impurity.

A solvent used in the isomerization reaction may be any solvent that has no adverse effect on the isomerization reaction. Examples of the solvent include water; alcoholic solvents such as methanol, ethanol, isopropyl alcohol, and t-butyl alcohol; ether solvents such as diethyl ether, di-n-butyl ether, di-t-butyl ether, tetrahydrofuran, 1,4-dioxane, and diethyleneglycol diethyl ether; hydrocarbon solvents such as hexane, heptane, benzene, toluene, and xylene; halogen-based solvents such as methylene chloride and chloroform; aprotic polar solvents such as N,N-dimethylformamide, N,N-dimethylacetamide, 1,3-dimethyl-2-imidazolidinone, dimethyl sulfoxide, and hexamethylphosphoric triamide; and nitrile solvents such as acetonitrile. The halogen-based solvents, the ether solvents, and the aprotic polar solvents are preferred in view of the reactivity.

The solvent may be used either alone or in combination thereof, if necessary, and may be optionally determined while considering the type and/or the reactivity and/or the selectivity of the (1,2-dimethyl-2,3-epoxycyclopentyl)acetate compound (6).

The solvent may be optionally determined while considering the reactivity and/or the solubility of the (1,2-dimethyl-2,3-epoxycyclopentyl)acetate compound (6), and the isomerization reaction may be carried out without a solvent.

An amount of the solvent is, for example, preferably from more than 0 g to 10,000 g per mol of the (1,2-dimethyl-2,3-epoxycyclopentyl)acetate compound (6), more preferably from 100 g to 5,000 g, in view of the reactivity and/or the economy.

A reaction temperature of the isomerization reaction may be optionally determined while considering the reactivity of the (1,2-dimethyl-2,3-epoxycyclopentyl)acetate compound (6) and/or the formation of an impurity and is, for example, preferably from −30° C. to 500° C., more preferably from 0° C. to 100° C., in view of the reactivity and/or the formation of an impurity.

The reaction time of the isomerization reaction is preferably optimized, depending on the reactivity of the (1,2-dimethyl-2,3-epoxycyclopentyl)acetate compound (6), by monitoring the reaction progress with, for example, gas chromatography and/or thin layer chromatography to confirm the disappearance of the (1,2-dimethyl-2,3-epoxycyclopentyl)acetate compound (6) and is, for example, preferably from 1 hour to 168 hours, more preferably from 1 hour to 24 hours, even more preferably from 1 hour to 12 hours, in view of the yield and/or the formation of an impurity.

The (1,2-dimethyl-3-oxocyclopentyl)acetate compound (7) formed in the isomerization reaction may be suitably isolated and/or purified in any purification method used in usual organic synthesis such as distillation at a reduced pressure and/or various chromatography. Distillation at a reduced pressure is preferred in view of the industrial economy. When the (1,2-dimethyl-3-oxocyclopentyl)acetate compound (7) formed in the isomerization reaction has a sufficient purity, the crude product comprising the (1,2-dimethyl-3-oxocyclopentyl)acetate compound (7) may be used as such without purification in a subsequent step.

C-3. Methylation Reaction

The (1,2-dimethyl-3-oxocyclopentyl)acetate compound (7), which is the starting material, will be described below.

The (1,2-dimethyl-3-methylenecyclopentyl)acetate compound (3) to be formed in the methylation reaction will be described below.

R in the general formula (3) is as defined for the general formula (1).

Examples of the (1,2-dimethyl-3-methylenecyclopentyl) acetate compound (3) include linear alkyl (1,2-dimethyl-3-methylenecyclopentyl)acetates such as methyl (1,2-dimethyl-3-methylenecyclopentyl)acetate, ethyl (1,2-dimethyl-3-methylenecyclopentyl)acetate, n-propyl (1,2-dimethyl-3-methylenecyclopentyl)acetate and n-butyl (1,2-dimethyl-3-methylenecyclopentyl)acetate; and branched alkyl (1,2-dimethyl-3-methylenecyclopentyl)acetates such as isopropyl (1,2-dimethyl-3-methylenecyclopentyl)acetate and isobutyl (1,2-dimethyl-3-methylenecyclopentyl)acetate.

Examples of the (1,2-dimethyl-3-methylenecyclopentyl) acetate compound (3) may be its enantiomers, diastereomers, and a mixture of such stereoisomers in the same or different amounts.

The methylation reaction be carried out using a known methylation reaction or a reaction which uses a methylenation reagent, and may be carried out with heating or cooling, if needed.

Examples of the methylation reaction or the reaction which uses the methylation reagent include the Wittig reaction which uses a ylide compound obtained from a base and a methyltriphenylphosphonium halide, a reaction which uses a Tebbe reagent prepared from titanocene chloride and trimethylaluminum, a reaction which uses a Petasis reagent prepared from titanocene chloride and methyl magnesium halide or methyllithium, a Johnson Olefination reaction which uses an anion obtained from a base and N-alkyl sulfoximine, a Julia-Kocienski Type reaction which uses an anion obtained from a base and 1-methyl-2-(methyl sulfonyl)benzimidazole, a Simmons-Smith reaction with a zinc-copper couple and diiodomethane, and a reaction with a dihalomethane such as dibromomethane or diiodomethane, zinc, titanium chloride (IV) or aluminum chloride (III).

The methylation reagent may be prepared by a known method, or, may be commercially available one.

The methylation reaction or the reaction which uses the methylation reagent is preferably a reaction which uses a Petasis reagent prepared from titanocene chloride and methyl magnesium halide or methyllithium, or a reaction with a dihalomethane such as dibromomethane or diiodomethane, zinc, titanium chloride (IV) or aluminum chloride (III) in view of the yield and/or reactivity, more preferably a reaction which uses a Petasis reagent.

The Petasis reagent specifically refers to a solution of dimethyltitanocene in tetrahydrofuran or a toluene, and methylenates a carbonyl group due to the formation of a carbene type active species by the thermal decomposition of dimethyltitanocene in the methylation reaction system.

For example, when the methylation reaction is carried out with the Petasis reagent, the amount of dimethyltitanocene is preferably from 1.0 mol to 5.0 mol, more preferably from 1.0 mol to 2.0 mol, per mol of the (1,2-dimethyl-3-oxocyclopentyl)acetate compound (7) in view of the economy and/or the yield.

Examples of the solvent used in the methylation with a Petasis reagent include ether solvents such as diethyl ether, di-n-butyl ether, di-t-butyl ether, tetrahydrofuran, 1,4-dioxane, and diethyleneglycol diethyl ether; hydrocarbon solvents such as hexane, heptane, benzene, toluene, and xylene; and halogen-based solvents such as methylene chloride and chloroform. Ether solvents and hydrocarbon solvent are preferable in view of the reactivity and/or the solubility.

The solvent may be used either alone or in combination thereof, if necessary, and may be optionally determined while considering the type and/or the reactivity and/or the selectivity of the (1,2-dimethyl-3-oxocyclopentyl)acetate compound (7).

An amount of the solvent may be optionally determined while considering the reactivity and/or the solubility of the (1,2-dimethyl-3-oxocyclopentyl)acetate compound (7). For example, an amount of the solvent is preferably 100 g to 10,000 g, more preferably from 500 g to 5,000 g, per mol of the (1,2-dimethyl-3-oxocyclopentyl)acetate compound (7) in view of the reactivity and/or the solubility.

A reaction temperature of the methylation reaction with the Petasis reagent is preferably no less than the temperature at which the dimethyltitanocene thermally decomposes and generates a carbene type active species, and may be determined while considering the reactivity of the (1,2-dimethyl-3-oxocyclopentyl) acetate compound (7) and/or the formation of an impurity, and preferred is for example from 50° C. to 200° C., more preferred is from 50° C. to 100° C., in view of the reactivity and/or the stability of the active species.

The reaction time of the methylation reaction with the Petasis reagent is preferably optimized, depending on the reactivity of the (1,2-dimethyl-3-oxocyclopentyl) acetate compound (7), by monitoring the reaction progress with, for example, gas chromatography and/or thin layer chromatography to confirm the disappearance of the (1,2-dimethyl-3-oxocyclopentyl) acetate compound (7), and is, for example, preferably from 1 hour to 168 hours, more preferably from 1 hour to 24 hours, even more preferably from 1 hour to 18 hours, in view of the yield and/or the formation of an impurity.

D. The process for preparing (1,2-dimethyl-3-methylenecyclopentyl)acetaldehyde of the following formula (4) will be described below.

(1,2-dimethyl-3-methylenecyclopentyl)acetaldehyde (4) may be prepared by converting an alkoxycarbonylmethyl group (i.e., —CH$_2$C(=O)OR) of the (1,2-dimethyl-3-methylenecyclopentyl)acetate compound (3) obtained in the aforesaid item C to a formylmethyl group (i.e., —CH$_2$CHO), as shown in the following reaction formula (see, for example, Example 3-1 to Example 3-3 below).

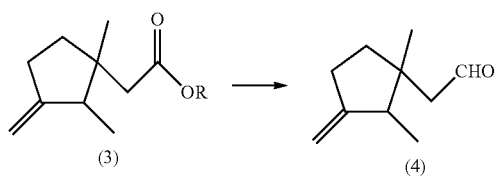

(3) → (4)

The (1,2-dimethyl-3-methylenecyclopentyl)acetate compound (3), which is the starting material, is as mentioned above.

Next, (1,2-dimethyl-3-methylenecyclopentyl)acetaldehyde (4) which may be prepared by the conversion of the functional group will be described below.

Examples of (1,2-dimethyl-3-methylenecyclopentyl)acetaldehyde (4) may be its enantiomers, diastereomers, and a mixture of such stereoisomers in the same or different amounts.

The converting the alkoxycarbonylmethyl group (i.e., —CH$_2$C(=O)OR) of the (1,2-dimethyl-3-methylenecyclopentyl)acetate compound (3) to a formylmethyl group (i.e., —CH$_2$CHO) may be carried out with a known method for converting a functional group or a combination of known methods for converting a functional group.

An example of one conversion method includes a single step method comprising subjecting the (1,2-dimethyl-3-methylenecyclopentyl)acetate compound (3) to a reduction reaction with a reducing agent to obtain (1,2-dimethyl-3-methylenecyclopentyl)acetaldehyde (4) (hereinafter, referred to as Preparation Process 1) as shown in the following reaction formula (for example, see Example 3-1 below).

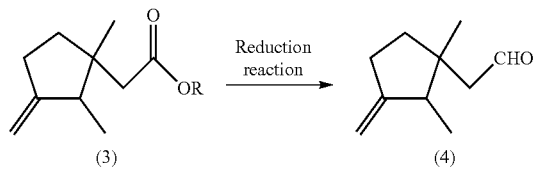

(3) → (4)

Another example of one conversion method includes a multiple step method comprising subjecting the (1,2-dimethyl-3-methylenecyclopentyl)acetate compound (3) to a reduction reaction with a reducing agent to obtain 2-(1,2-dimethyl-3-methylenecyclopentyl)ethyl alcohol (8), and then, subjecting 2-(1,2-dimethyl-3-methylenecyclopentyl)ethyl alcohol (8) thus obtained to an oxidation reaction with an oxidizing agent to obtain (1,2-dimethyl-3-methylenecyclopentyl)acetaldehyde (4) (hereinafter, referred to as Preparation Process 2), as shown in the following reaction formula (see, for example, Example 3-2 and Example 3-3 below).

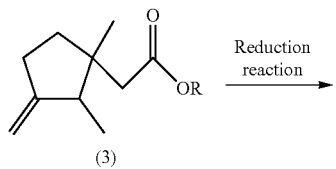

(3)

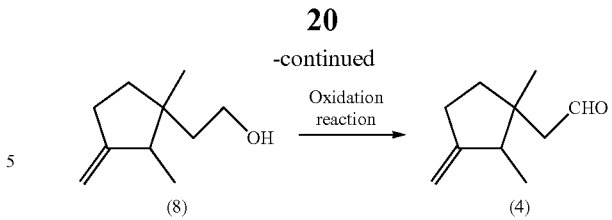

(8) → (4)

(a) The Preparation Process 1 will be described below.

The reduction reaction of the (1,2-dimethyl-3-methylenecyclopentyl)acetate compound (3) with a reducing agent to form (1,2-dimethyl-3-methylenecyclopentyl)acetaldehyde (4) may be carried out with a known method, and may be carried out with heating or cooling, if needed.

The reducing agent used in the reduction reaction may be a known reducing agent and is not specifically limited.

Examples of the reducing agent include metal hydrides such as aluminum hydride, alkylaluminum hydride, dialkylaluminum hydride, sodium hydride, lithium hydride, potassium hydride, and calcium hydride; and metal hydride complexes such as sodium borohydride, lithium borohydride, potassium borohydride, sodium trimethoxyborohydride, lithium triethylborohydride, sodium aluminum hydride, lithium aluminum hydride, lithium trimethoxyaluminum hydride, lithium diethoxyaluminum hydride, lithium tri-t-butoxyaluminum hydride, and sodium bis(2-methoxyethoxy)aluminum hydride. The metal hydride complexes are preferred in view of the reactivity and/or the yield.

Depending on the type of the reducing agent, the reduction reaction may be carried out in the presence of an excess of a dialkylamine such as diethylamine to reduce 2-(1,2-dimethyl-3-methylenecyclopentyl)ethyl alcohol which is produced as by-product by an over-reduction reaction.

An amount of the reducing agent in the reduction reaction may be arbitrarily set depending on the reactivity of the reducing agent and/or the structure of the reducing agent and/or the reaction mechanism and is, for example, preferably from 0.2 mol to 5.0 mol, more preferably from 0.25 mol to 2.0 mol, per mol of the (1,2-dimethyl-3-methylenecyclopentyl)acetate compound (3) in view of the reactivity and/or the yield.

A solvent used in the reduction reaction may be any solvent that has no adverse effect on the reduction reaction. Examples of the solvent used in the reduction reaction include water; hydrocarbon solvents such as hexane, heptane, octane, benzene, toluene and xylene; ether solvents such as diethyl ether, dibutyl ether, cyclopentyl methyl ether, diethyleneglycol diethyl ether, diethyleneglycol dimethyl ether, tetrahydrofuran, and 1,4-dioxane; halogen-based solvents such as methylene chloride and chloroform; alcoholic solvents such as methanol, ethanol, 1-propanol, and 2-propanol; nitrile solvents such as acetonitrile; and aprotic polar solvents such as N,N-dimethylformamide, N,N-dimethylacetamide, dimethyl sulfoxide, and hexamethylphosphoric triamide.

The solvent may be used either alone or in combination thereof, if necessary, and may be optionally determined while considering the type and/or the reactivity of the (1,2-dimethyl-3-methylenecyclopentyl)acetate compound (3).

An amount of solvent used in the reduction reaction may be optionally determined while considering the reactivity and/or the solubility of the (1,2-dimethyl-3-methylenecyclopentyl)acetate compound (3) and is, for example, preferably from 100 g to 20,000 g, more preferably from 200 g to 10,000 g, per mol of the (1,2-dimethyl-3-methylenecyclopentyl)acetate compound (3) in view of the reactivity and/or the economy.

The temperature of the reduction reaction may be carried out at a reaction temperatures that do not adversely affect the reduction reaction, and is preferably from −76° C. to 100° C., more preferably from −76° C. to −30° C., in view of yield and/or the by-product formation.

The reaction time of the reduction reaction is preferably optimized, depending on the reactivity of the (1,2-dimethyl-3-methylenecyclopentyl)acetate compound (3), by monitoring the reaction progress with, for example, gas chromatography and/or thin layer chromatography to confirm the disappearance of the (1,2-dimethyl-3-methylenecyclopentyl)acetate compound (3), and is, for example, preferably from 1 hour to 168 hours, more preferably from 1 hour to 12 hours, even more preferably from 1 hour to 6 hours, in view of the yield and/or the formation of an impurity.

(1,2-Dimethyl-3-methylenecyclopentyl)acetaldehyde (4) formed in the reduction reaction may be suitably isolated and/or purified in any purification method used in usual organic synthesis such as distillation at a reduced pressure and/or various chromatography. Distillation at a reduced pressure is preferred in view of the industrial economy. When (1,2-dimethyl-3-methylenecyclopentyl)acetaldehyde (4) formed in the reduction reaction has a sufficient purity, the crude product comprising (1,2-dimethyl-3-methylenecyclopentyl)acetaldehyde (4) may not need to be purified.

(b) Next, the Preparation Process 2 will be described.

The reduction reaction of the (1,2-dimethyl-3-methylenecyclopentyl)acetate compound (3) with a reducing agent to form 2-(1,2-dimethyl-3-methylenecyclopentyl)ethyl alcohol (8) may be carried out with a known method, and may be carried out with heating or cooling, if needed.

The reducing agent used in the reduction reaction may be a known reducing agent and is not specifically limited.

Examples of the reducing agent include hydrogen; boron compounds such borane, alkylborane, dialkylborane, and bis(1,2-dimethylpropyl) borane; metal hydrides such as dialkylsilane, trialkylsilane, aluminum hydride, alkylaluminum hydride, dialkylaluminum hydride, sodium hydride, lithium hydride, potassium hydride, and calcium hydride; and metal hydride complexes such as sodium borohydride, lithium borohydride, potassium borohydride, sodium trimethoxyborohydride, lithium triethylborohydride, sodium aluminum hydride, lithium aluminum hydride, lithium trimethoxyaluminum hydride, lithium diethoxyaluminum hydride, lithium tri-t-butoxyaluminum hydride, and sodium bis(2-methoxyethoxy)aluminum hydride. The metal hydride complexes are preferred in view of the reactivity and/or the yield.

An amount of the reducing agent in the reduction reaction may be arbitrarily set depending on the reactivity of the reducing agent and/or the structure of the reducing agent and/or the reaction mechanism and is, for example, preferably from 0.2 mol to 10.0 mol, more preferably from 0.25 mol to 5.0 mol, per mol of the (1,2-dimethyl-3-methylenecyclopentyl)acetate compound (3) in view of the reactivity and/or the economy.

The solvent used in the reduction reaction is the same as the solvent used in the reduction reaction of Preparation Process 1.

The solvent may be used either alone or in combination thereof, if necessary, and may be optionally determined while considering the type and/or the reactivity of the (1,2-dimethyl-3-methylenecyclopentyl)acetate compound (3).

An amount of solvent used in the reduction reaction may be optionally determined while considering the reactivity and/or the solubility of the (1,2-dimethyl-3-methylenecyclopentyl)acetate compound (3) and is, for example, preferably from 30 g to 10,000 g, more preferably from 100 g to 6,000 g, per mol of the (1,2-dimethyl-3-methylenecyclopentyl)acetate compound (3) in view of the reactivity and/or the economy.

The temperature of the reduction reaction may be carried out at a reaction temperatures that do not adversely affect the reduction reaction, and is preferably from −50° C. to 150° C., more preferably from −25° C. to 80° C., in view of yield and/or the by-product formation.

The reaction time of the reduction reaction is preferably optimized, depending on the reactivity of the (1,2-dimethyl-3-methylenecyclopentyl)acetate compound (3), by monitoring the reaction progress with, for example, gas chromatography and/or thin layer chromatography to confirm the disappearance of the (1,2-dimethyl-3-methylenecyclopentyl)acetate compound (3), and is, for example, preferably from 1 hour to 168 hours, more preferably from 1 hour to 24 hours, even more preferably from 1 hour to 12 hours, in view of the yield and/or the formation of an impurity.

2-(1,2-Dimethyl-3-methylenecyclopentyl)ethyl alcohol (8) formed in the reduction reaction may be suitably isolated and/or purified in any purification method used in usual organic synthesis such as distillation at a reduced pressure and/or various chromatography. Distillation at a reduced pressure is preferred in view of the industrial economy. When 2-(1,2-dimethyl-3-methylenecyclopentyl)ethyl alcohol (8) formed in the reduction reaction has a sufficient purity, the crude product comprising 2-(1,2-dimethyl-3-methylenecyclopentyl)ethyl alcohol (8) may be used as such without purification in a subsequent step.

Examples of 2-(1,2-dimethyl-3-methylenecyclopentyl)ethyl alcohol (8) to be formed in the reduction reaction may be its enantiomers, diastereomers, and a mixture of such stereoisomers in the same or different amounts.

Next, the oxidation reaction of 2-(1,2-dimethyl-3-methylenecyclopentyl)ethyl alcohol (8) with an oxidizing agent to form (1,2-dimethyl-3-methylenecyclopentyl)acetaldehyde (4) may be a known method, and may be carried out with heating or cooling, if needed.

The oxidizing agent used in the oxidation reaction may be a known oxidizing agent and is not specifically limited.

Examples of the oxidizing agent include hypervalent iodine compounds, chromium acid compounds, sulfoxide compounds, manganese compounds, nitroxyl radical compounds, and ruthenic acid compounds.

Examples of the hypervalent iodine compound include 2-iodoxybenzoic acid, 1,1,1-triacetoxy-1,1-dihydro-1,2-benzoiodoxol-3 (1H)-one, and 2-iodoxy-5-methylbenzenesulfonic acid.

2-Iodoxy-5-methylbenzenesulfonic acid may be prepared, for example, by reacting potassium 2-iodo-5-methylbenzenesulfonate with a monopersulfate salt such as potassium monopersulfate.

Examples of the chromium acid compound include chromium trioxide pyridine complex, pyridinium chlorochromate, pyridinium dichromate, and chromic acid ester.

Examples of the sulfoxide compound include dimethyl sulfoxide, methyl ethyl sulfoxide, methyl propyl sulfoxide, methyl dodecyl sulfoxide, methyl 1-methylethyl sulfoxide, methyl 1-methylpropyl sulfoxide, methyl 1,1-dimethylethyl sulfoxide, methyl phenyl sulfoxide, and methyl benzyl sulfoxide.

Examples of the manganese compound include manganese dioxide and barium manganate.

Examples of the nitroxyl radical compound include 2,2,6,6-tetramethylpiperidine-1-oxyl, 4-hydroxy-2,2,6,6-tetramethylpiperidine-1-oxyl, 2-azaadamantane-N-oxyl, 1-methyl-2-azaadamantane-N-oxyl, and 9-azaadamantane-N-oxyl.

Examples of the ruthenic acid compound include ammonium perruthenate compounds such as tetrapropylammonium perruthenate.

Sulfoxide compounds and nitroxyl radical compounds are preferably as the oxidizing agent in view of the yield and/or the selectivity.

An amount of the oxidizing agent is preferably from 1.0 mol to 80.0 mol, more preferably from 1.5 mol to 50.0 mol, per mol of 2-(1,2-dimethyl-3-methylenecyclopentyl)ethyl alcohol (8) in view of the reactivity and/or the yield.

The oxidizing agent may be used either alone or in combination thereof, if necessary. The oxidizing agent may be a commercially available one.

When a nitroxyl radical compound is used as the oxidizing agent, hypochlorite or iodobenzene diacetate may be used as the re-oxidizing agent, if necessary, and when a ruthenic acid compound is used as the oxidizing agent, amine oxide compounds such as N-methylmorpholine oxide may be used as a re-oxidizing agent, if necessary.

When a sulfoxide compound is used as the oxidizing agent, an activator is preferably used.

Examples of the activator include sulfur trioxide complexes such as sulfur trioxide pyridine complex, sulfur trioxide triethylamine complex, and sulfur trioxide trimethylamine complex; acid anhydrides such as acetic anhydride and trifluoroacetic anhydride; carbodiimide compounds such as dicyclohexylcarbodiimide, diisopropylcarbodiimide, and 1-ethyl-3-(3-dimethylaminopropyl) carbodiimide hydrochloride; acid chlorides such as oxalyl chloride, and thionyl chloride; chlorine, and phosphorus pentoxide.

An amount of the activator is preferably from 1.0 mol to 10.0 mol, more preferably from 2.0 mol to 5.0 mol, per mol of 2-(1,2-dimethyl-3-methylenecyclopentyl)ethyl alcohol (8) in view of the reactivity and/or the yield.

When a sulfur trioxide complex, an acid anhydride, a carbodiimide compound, oxalyl chloride, chlorine or phosphorus pentoxide is used as the activator, a base is preferably further used.

Examples of the base include trialkylamine compounds such as trimethylamine, triethylamine, tripropylamine, tributylamine, trioctylamine, tridodecylamine, and diisopropylethylamine; and cyclic tertiary amine compounds such as N-methyl piperidine, N-ethyl piperidine, N-methyl pyrrolidine, and N-ethyl pyrrolidine. Trimethylamine, triethylamine and tripropylamine are preferred in view of the cost and/or the ease of availability and/or the reactivity.

An amount of the base is preferably from 1.0 mol to 10.0 mol, more preferably from 3.0 mol to 6.0 mol, per mol of 2-(1,2-dimethyl-3-methylenecyclopentyl)ethyl alcohol (8) in view of the reactivity and/or the yield.

When a carbodiimide compound is used as the activator, an acid may be used together with the base.

Examples of the acid include trifluoroacetic acid, difluoroacetic acid, trichloroacetic acid, dichloroacetic acid, monochloroacetic acid, cyanoacetic acid, orthophosphoric anhydride, and phosphorous acid. Trifluoroacetic acid, dichloroacetic acid and orthophosphoric anhydride are preferred in view of the reactivity.

The acid may be used either alone or in combination thereof, if necessary. The acid may be a commercially available one.

The amount of acid is preferably from 0.3 mol to 2.0 mol, more preferably from 0.3 mol to 1.0 mol, per mol of 2-(1,2-dimethyl-3-methylenecyclopentyl)ethyl alcohol (8) in view of the reactivity or the amount of generated by-product.

A solvent may be used in the oxidation reaction, if necessary.

A solvent used in the oxidation may be any solvent that has no adverse effect on the oxidation reaction. Examples of the solvent used in the oxidation reaction include halogen-based solvents such as methylene chloride, chloroform, carbon tetrachloride, trichloroethane, and tetrachloroethane; hydrocarbon solvents such as pentane, hexane, heptane, and cyclohexane; and aprotic polar solvents such as N,N-dimethylformamide, N,N-dimethylacetamide, dimethyl sulfoxide, and hexamethylphosphoric triamide. Methylene chloride, chloroform, and N,N-dimethylformamide are preferred in view of the reactivity and/or the yield.

When a sulfoxide compound is used as the oxidizing agent, the sulfoxide compound itself may be used as the solvent, and when a base is sued, the base itself may be used as the solvent.

An amount of the solvent is preferably from 100 g to 10,000 g, more preferably from 1,000 g to 8,000 g, per mol of 2-(1,2-dimethyl-3-methylenecyclopentyl)ethyl alcohol (8) in view of the economy and/or the reactivity.

The solvent may be used either alone or in combination thereof, if necessary, and may be optionally determined while considering the type and/or the reactivity of 2-(1,2-dimethyl-3-methylenecyclopentyl)ethyl alcohol (8).

The temperature of the oxidation reaction is preferably from −50° C. to 80° C., more preferably from 0° C. to 50° C., in view of the reaction rate and/or the yield.

The reaction time of the oxidation reaction is preferably optimized, depending on the reactivity of 2-(1,2-dimethyl-3-methylenecyclopentyl)ethyl alcohol (8), by monitoring the reaction progress with, for example, gas chromatography and/or thin layer chromatography to confirm the disappearance of 2-(1,2-dimethyl-3-methylenecyclopentyl)ethyl alcohol (8), and is, for example, preferably from 1 hour to 168 hours, more preferably from 1 hour to 24 hours, even more preferably from 1 hour to 12 hours, in view of the yield and/or the formation of an impurity.

(1,2-Dimethyl-3-methylenecyclopentyl)acetaldehyde (4) formed in the oxidation reaction may be suitably isolated and/or purified in any purification method used in usual organic synthesis such as distillation at a reduced pressure and/or various chromatography. Distillation at a reduced pressure is preferred in view of the industrial economy. When (1,2-dimethyl-3-methylenecyclopentyl)acetaldehyde (4) formed in the oxidation reaction has a sufficient purity, the crude product comprising (1,2-dimethyl-3-methylenecyclopentyl)acetaldehyde (4) may not need to be purified.

As stated above, the (1,2-dimethyl-2-cyclopentenyl)acetate compound (2) may be obtained in an industrially readily applicable range of the reaction temperature without an ignitable starting material and an industrially expensive starting material by subjecting the haloacetaldehyde alkyl 2,3-dimethyl-2-cyclopentenyl acetal compound (1) to a dehydrohalogenation reaction in the presence of a base, followed by a rearrangement reaction to obtain the (1,2-dimethyl-2-cyclopentenyl)acetate compound (2), and subjecting the (1,2-dimethyl-2-cyclopentenyl)acetate compound (2) thus obtained to an epoxidation reaction, followed by an isomerization reaction, and then a methylenation reaction to industrially and economically obtain the (1,2-dimethyl-3-methylenecyclopentyl)acetate compound (3). Subsequently, (1,2-dimethyl-3-methylenecyclopentyl)acetaldehyde (4) may be industrially and economically prepared by converting an alkoxycarbonylmethyl group (i.e., —CH$_2$C(=O)OR) of the obtained (1,2-dimethyl-3-methylenecyclopentyl)acetate compound (3) to a formylmethyl group (i.e., —CH$_2$CHO).

EXAMPLES

The present invention will be described with reference to the following Examples and Comparative Examples. It should be construed that the present invention is not limited to or by the Examples.

The term "purity" as used herein means an area percentage obtained by gas chromatography (hereinafter referred to also as "GC"), unless otherwise specified. The term "product ratio" means a ratio of area percentages in GC.

The term "yield" is calculated from the area percentages determined by GC.

The yield was calculated by the following equation in consideration of purities (% GC) of a starting material and a product.

Yield (%)=[(mass of a product obtained in a reaction×% GC)/molecular mass of a product]÷[(mass of a starting material×% GC)/molecular mass of a starting material]}×100

GC Conditions were as Follows:

GC conditions for determination of "purity" and "product ratio": GC: Capillary gas chromatograph GC-2010 (Shimadzu Corporation); column: DB-5, 0.25 μm×0.25 mmϕ×30 m, carrier gas: He (1.55 mL/min); detector: FID; column temperature: 60° C., kept for 3 minutes, elevated by 10° C./min, up to 230° C.

As used herein, Et represents an ethyl group, $^i$Pr represents an isopropyl group, and $^n$Bu represents an n-butyl group.

SYNTHESIS EXAMPLE

The following Synthesis Example 1 describes the process for preparing the haloacetaldehyde alkyl 2,3-dimethyl-2-cyclopentenyl acetal compound (1), as shown in the following reaction formula.

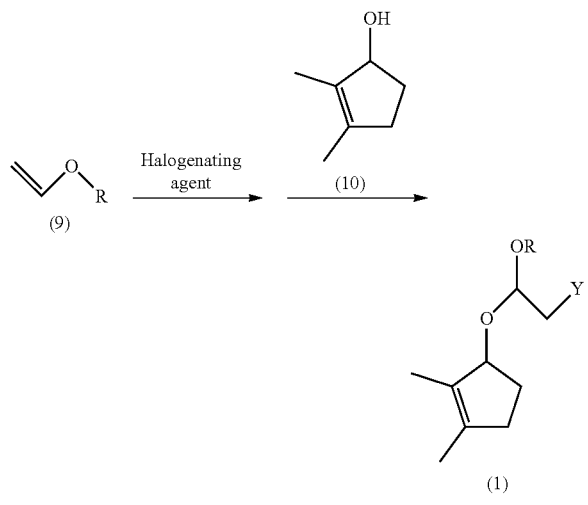

Synthesis Example 1

Preparation of bromoacetaldehyde 2,3-dimethyl-2-cyclopentenyl ethyl acetal (1: R=Et; Y=Br)

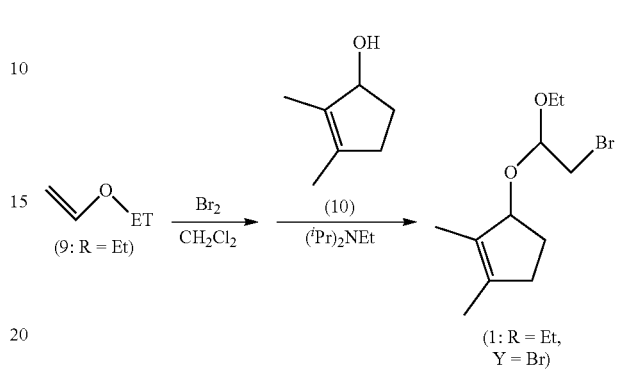

Air in a reactor equipped with a stirrer, a condenser, and a thermometer was purged with nitrogen. Then, to the reactor were added bromine (Br$_2$) (26.36 g: 0.165 mol) and methylene chloride (CH$_2$Cl$_2$) (750.0 g), and the liquid temperature was lowered to −5° C. to 0° C. Ethyl vinyl ether (9: R=Et) (12.98 g: 0.180 mol) was added dropwise to the mixture whose temperature was maintained at a liquid temperature of −5° C. to 0° C. over 90 minutes. After the completion of the dropwise addition, the reaction mixture was stirred at a liquid temperature of −5° C. to 0° C. for 30 minutes. After the completion of the stirring, diisopropylethylamine (($^i$Pr)$_2$NEt) (23.27 g: 0.180 mol) was added at a liquid temperature of −5° C. to 0° C. over 10 minutes. After the completion of the addition, 2,3-dimethyl-2-cyclopenten-1-ol (10) (16.83 g: 0.150 mol, purity 93.6%) was added dropwise at a liquid temperature of −10° C. to −5° C. over one hour. After the completion of the dropwise addition, the reaction mixture was stirred at a liquid temperature of −5° C. to 0° C. for one hour, and then at a liquid temperature of 20° C. to 25° C. for three hours.

After the stirring, an aqueous 3.5 wt % sodium bicarbonate solution (500.0 g) was added to the reaction mixture to quench the reaction. After the quenching of the reaction, the reaction mixture was separated into an organic layer and an aqueous layer, and the resulting organic layer was washed with water (300.0 g) and with an aqueous 10.0 wt % sodium chloride solution (300.0 g) in this order. The solvent was removed from the washed organic layer at a reduced pressure, and then the crude product was purified by distillation at a reduced pressure to obtain bromoacetaldehyde 2,3-dimethyl-2-cyclopentenyl ethyl acetal (1: R=Et; Y=Br) (33.79 g: 0.128 mol, yield 85.3%, purity 87.8%).

The following are various spectrum data of bromoacetaldehyde 2,3-dimethyl-2-cyclopentenyl ethyl acetal (1: R=Et; Y=Br) thus prepared.

Nuclear magnetic resonance spectrum: $^1$H-NMR (500 MHz, CDCl$_3$): δ 1.12 (1.5H, t, J=7.2 Hz), 1.14 (1.5H, t, J=6.9 Hz), 1.60-1.62 (6H, m), 1.63-1.70 (1H, m), 2.03-2.15 (2H, m), 2.30 (1H, br), 3.41-3.49 (2H, m), 3.51-3.65 (2H, m), 4.47 (0.5H, br), 4.55 (0.5H, br), 4.68 (0.5H, t, J=5.4 Hz), 4.70 (0.5H, t, J=5.4 Hz) ppm. $^{13}$C-NMR (126 MHz, CDCl$_3$): δ 11.30, 11.31, 13.95, 15.15, 15.23, 28.9, 29.87, 33.36, 33.46, 35.07, 35.18, 60.78, 61.32, 85.30, 86.78, 99.53, 101.37, 130.83, 131.33, 135.27, 135.81 ppm.

Mass spectrum EI (70 eV): m/z 152, 149, 137, 123, 121, 111, 95, 94, 79, 72, 55, 42, 29.

Infrared absorption spectrum (D-ATR): ν (cm$^{-1}$) 683, 1031, 1056, 1113, 1185, 1336, 1381, 1422, 1442, 2849, 2913, 2974.

Example 1

The following Example 1-1 describes a process for preparing the (1,2-dimethyl-2-cyclopentenyl)acetate compound (2) from the haloacetaldehyde alkyl 2,3-dimethyl-2-cyclopentenyl acetal compound (1), as shown in the following reaction formula.

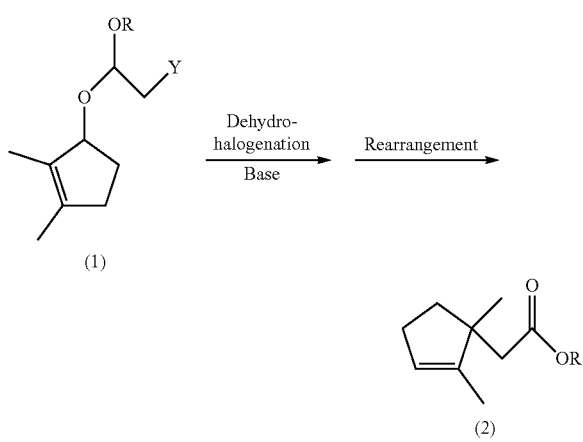

Example 1-1

Preparation of ethyl (1,2-dimethyl-2-cyclopentenyl)acetate (2: R=Et)

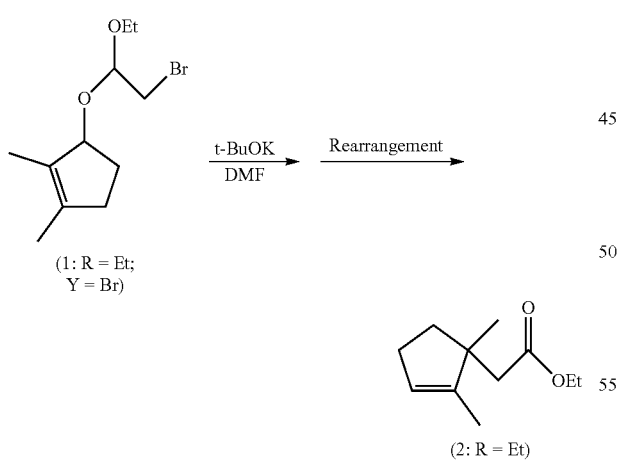

Air in a reactor equipped with a stirrer, a condenser, and a thermometer was purged with nitrogen. Then, to the reactor were added bromoacetaldehyde 2,3-dimethyl-2-cyclopentenyl ethyl acetal (1: R=Et; Y=Br) (26.32 g: 0.100 mol, purity 87.9%) obtained in Synthesis Example 1 and N,N-dimethylformamide (DMF) (280.0 g), and then cooled to a liquid temperature of 0° C. to 5° C. Potassium t-butoxide (t-BuOK) (12.34 g: 0.110 mol) was added to the mixture whose temperature was maintained at a liquid temperature of 0° C. to 5° C. over 30 minutes. After the completion of the addition, the reaction was allowed at a liquid temperature of 20 to 25° C. for 4 hours.

After the reaction, the reaction mixture was heated to 100° C. and stirred for 5 hours. After the completion of the stirring, the reaction mixture was cooled to 0° C. to 5° C., and water (250.0 g) was added to the reactor to quench the reaction. Diethyl ether (300.0 g) was further added to the reactor to extract and separate the mixture into an organic layer and an aqueous layer. The organic layer was washed with an aqueous 10 wt % sodium chloride solution (300.0 g). The solvent was removed from the washed organic layer at a reduced pressure, and the crude product was then purified by silica gel column chromatography to obtain ethyl (1,2-dimethyl-2-cyclopentenyl)acetate (2: R=Et) (15.13 g: 0.083 mol, yield 83.0%, purity 97.3%).

The following are various spectrum data of ethyl (1,2-dimethyl-2-cyclopentenyl)acetate (2: R=Et) thus prepared.

Nuclear magnetic resonance spectrum: $^{1}$H-NMR (500 MHz, CDCl$_3$): δ 1.09 (3H, s), 1.24 (3H, t, J=7.2 Hz), 1.63 (3H, q, J=1.6 Hz), 1.67-1.72 (1H, m), 2.1-2.15 (1H, m), 2.17-2.21 (2H, m), 2.21 (1H, d, J=13.2 Hz), 2.33 (1H, d, J=13.2), 4.05-4.14 (2H, m), 5.29 (1H, br s, J=1.2 Hz) ppm. $^{13}$C-NMR (126 MHz, CDCl$_3$): δ 12.49, 14.40, 25.08, 29.32, 37.12, 43.59, 48.59, 60.12, 124.71, 145.56, 172.53 ppm.

Mass spectrum EI (70 eV): m/z 182 (M$^+$), 136, 94, 92, 78, 77, 67, 55, 53, 41, 39, 29.

Infrared absorption spectrum (D-ATR): ν (cm$^{-1}$) 799, 1036, 1096, 1129, 1171, 1216, 1284, 1315, 1367, 1446, 1733, 2852, 2934, 2961, 3039.

Example 2

The following Example 2-1 to Example 2-3 describe processes for preparing the (1,2-dimethyl-3-methylenecyclopentyl)acetate compound (3) from the (1,2-dimethyl-2-cyclopentenyl)acetate compound (2), as shown in the following reaction formula.

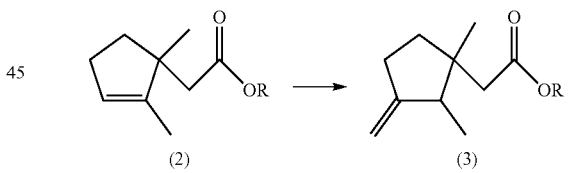

Example 2-1

Preparation of ethyl (1,2-dimethyl-2,3-epoxycyclopentyl)acetate (6: R=Et)

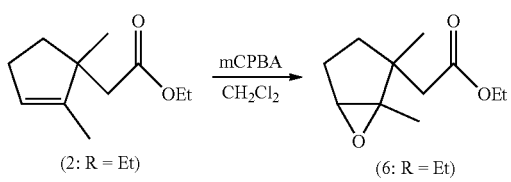

Air in a reactor equipped with a stirrer, a condenser, and a thermometer was purged with nitrogen. Then, to the reactor were added ethyl (1,2-dimethyl-2-cyclopentenyl) acetate (2: R=Et) (27.34 g: 0.150 mol, purity 97.3%) obtained in Example 1-1 and methylene chloride (CH$_2$Cl$_2$) (500.0 g), and the liquid temperature was lowered to −5° C. to 0° C. m-Chloroperoxybenzoic acid (mCPBA) (31.06 g: 0.180 mol, purity 65%) was added to the mixture whose temperature was maintained at a liquid temperature of −5° C. to 0° C. over two hours. After the completion of the addition, the reaction mixture was stirred at a liquid temperature of 0° C. to 5° C. for one hour. After the completion of the stirring, the by-product m-chlorobenzoic acid was filtered off, and then the filtrate was washed with 10 wt % sodium thiosulfate (300.0 g), and separated in an organic layer and an aqueous layer. The organic layer was washed with an aqueous 7 wt % sodium bicarbonate solution (300.0 g) and an aqueous 25.0 wt % sodium chloride solution (300.0 g) in this order. The solvent was removed from the washed organic layer at a reduced pressure to obtain ethyl (1,2-dimethyl-2,3-epoxycyclopentyl)acetate (6: R=Et) (29.23 g: 0.147 mol, yield 98.3%, purity 95.8%). Ethyl (1,2-dimethyl-2,3-epoxycyclopentyl) acetate (6: R=Et) thus obtained had a purity so as to allow the product to be used as such without purification in the subsequent process.

It was verified from the gas chromatography analysis that ethyl (1,2-dimethyl-2,3-epoxycyclopentyl)acetate (6: R=Et) thus prepared has two types of diastereomers [Diastereomer product ratio=41.1 (GC Retention time 13.11 minutes): 58.9 (GC Retention time 13.42 minutes)] at Retention time 13.11 minutes and Retention time 13.42 minutes, respectively. The above yields of ethyl (1,2-dimethyl-2,3-epoxycyclopentyl) acetate (6: R=Et) are represented as a mixture of the two types of diastereomers.

The following are various spectrum data of ethyl (1,2-dimethyl-2,3-epoxycyclopentyl)acetate (6: R=Et) thus prepared.

Nuclear magnetic resonance spectrum: $^1$H-NMR (600 MHz, DMSO-d$_6$): δ 0.99 (1.7H, s), 1.05 (1.3H, s), 1.08-1.10 (0.4H, m), 1.16-12.0 (3.0H, m), 125-129 (3.6H, m), 1.36-1.40 (0.6H, m), 1.58-1.69 (1.4H, m), 1.71-1.78 (1.0H, m), 2.23-2.27 (1.4H, m), 2.37 (0.6H, d, J=13.2 Hz), 3.28 (0.6H, s), 3.29 (0.4H, s), 4.02-4.07 (2.0H, m) ppm. $^{13}$C-NMR (150 MHz, DMSO-d$_6$): δ 12.61, 12.74, 14.08, 20.50, 21.43, 24.79, 25.20, 31.45, 32.27, 40.33, 40.60, 42.08, 42.22, 59.61, 59.80, 62.55, 63.44, 67.50, 67.61, 171.12, 171.39 ppm.

Mass spectrum EI (70 ev) GC Retention time 13.11 minutes: m/z 198 (M$^+$), 183, 153, 141, 125, 111, 110, 109, 95, 81, 69, 67, 55, 43, 29. GC Retention time 13.42 minutes: m/z 198 (M$^+$), 183, 153, 141, 125, 111, 110, 109, 95, 81, 69, 67, 55, 43, 29.

Infrared absorption spectrum (D-ATR): ν (cm$^{-1}$)669, 837, 914, 1032, 1096, 1116, 1180, 1222, 1261, 1369, 1453, 1733, 2876, 2936, 2965.

In order to determine the relative configuration of the two types of diastereomers of ethyl (1,2-dimethyl-2,3-epoxycyclopentyl)acetate (6: R=Et) thus prepared, the two dimensional NOESY spectrum was measured, and the Nuclear Overhauser effect (NOE) correlation was verified. As a result, the difference of the correlation between the two types of diastereomers was unclear. Therefore, it was difficult to consider the relative configuration.

Example 2-2

Preparation of ethyl (1,2-dimethyl-3-oxocyclopentyl)acetate (7: R=Et)

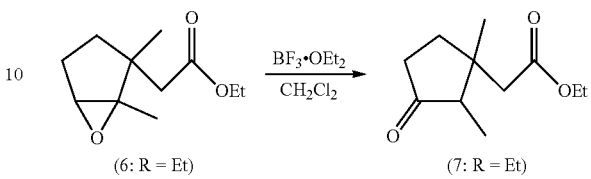

Air in a reactor equipped with a stirrer, a condenser, and a thermometer was purged with nitrogen. Then, to the reactor were added a boron trifluoride diethyl ether complex (BF$_3$·OEt) (4.54 g: 0.032 mol) and methylene chloride (CH$_2$Cl$_2$) (350.0 g), and then cooled to a liquid temperature of −5° C. to 0° C. Ethyl (1,2-dimethyl-2,3-epoxycyclopentyl)acetate (6: R=Et) (19.83 g: 0.100 mol, purity 95.8%) [Diastereomer product ratio=41.1 (GC Retention time 13.11 minutes): 58.9 (GC Retention time 13.42 minutes)] obtained in Example 2-1 and a methylene chloride (100.0 g) solution were added dropwise to the mixture whose temperature was maintained at a liquid temperature of 5° C. to 10° C. over one hour. After the completion of the dropwise addition, the reaction mixture was stirred at a liquid temperature of 5° C. to 10° C. for one hour, and them, a saturated aqueous sodium bicarbonate solution (150.0 g) was added to the reaction mixture to quench the reaction. After the quenching of the reaction, the reaction mixture was stirred at liquid temperature of 20° C. to 25° C. for an additional hour, and was separated into an organic layer and an aqueous layer. The resulting organic layer was washed with a saturated sodium chloride solution (300.0 g), and the solvent was removed from the washed organic layer at a reduced pressure to obtain ethyl (1,2-dimethyl-3-oxocyclopentyl)acetate (7: R=Et) (19.47 g: 0.098 mol, yield 98.2%, purity 96.1%). Ethyl (1,2-dimethyl-3-oxocyclopentyl)acetate (7: R=Et) thus obtained had a purity so as to allow the product to be used as such without purification in the subsequent process.

It was verified from the gas chromatography analysis that ethyl (1,2-dimethyl-3-oxocyclopentyl)acetate (7: R=Et) thus prepared has two types of diastereomers [Diastereomer product ratio=53.6 (GC Retention time 14.40 minutes): 46.4 (GC Retention time 14.60 minutes)] at Retention time 14.40 minutes and Retention time 14.60 minutes, respectively. The above yields of ethyl (1,2-dimethyl-3-oxocyclopentyl)acetate (7: R=Et) are represented as a mixture of the two types of diastereomers.

The following are various spectrum data of ethyl (1,2-dimethyl-3-oxocyclopentyl)acetate (7: R=Et) thus prepared.

Nuclear magnetic resonance spectrum: $^1$H-NMR (600 MHz, CDCl$_3$): δ 0.89 (1.5H, s), 0.96 (1.5H, d, J=7.2 Hz), 0.98 (1.5H, d, J=7.2 Hz), 1.25 (1.5H, s), 1.24-12.8 (4.5H, m), 1.64-1.68 (0.5H, m), 1.93-1.96 (1H, m), 1.99-2.04 (1H, m), 2.12-2.26 (2.5H, m), 2.29-2.36 (1.5H, m), 2.48 (0.5H, d, J=14.4 Hz), 4.09-4.18 (2.0H, m) ppm. $^{13}$C-NMR (150 MHz, CDCl$_3$): δ 7.81, 8.24, 14.24, 14.29, 19.68, 25.79, 32.09, 33.03, 34.78, 34.92, 38.87, 41.11, 41.51, 45.08, 53.73, 55.96, 60.33, 60.38, 171.46, 171.80, 219.41, 219.94 ppm.

Mass spectrum EI (70 ev) GC Retention time 14.40 minutes: m/z 198 (M$^+$), 183, 170, 153, 141, 124, 111, 96, 83, 69, 55, 41, 29. GC Retention time 14.60 minutes: m/z 198 (M$^+$), 183, 170, 153, 141, 124, 111, 96, 83, 69, 55, 41, 29.

Infrared absorption spectrum (D-ATR): ν (cm$^{-1}$) 1034, 1098, 1117, 1209, 1239, 1294, 1337, 1370, 1412, 1455, 1737, 2877, 2938, 2971.

In order to determine the relative configuration of the two types of diastereomers of ethyl (1,2-dimethyl-3-oxocyclopentyl)acetate (7: R=Et) thus prepared, the two dimensional NOESY spectrum was measured, and the Nuclear Overhauser effect (NOE) was verified. The results are shown below. Note that, the NOE is indicated by both arrows.

It is thought that the diastereomer detected at the GC Retention time 14.40 minutes is the following (1R*,2S*)-ethyl(1,2-dimethyl-3-oxocyclopentyl)acetate, and

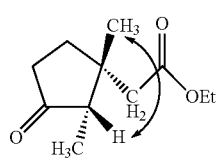

the diastereomer detected at the GC Retention time 14.60 minutes is the following (1R*, 2R*)-ethyl(1,2-dimethyl-3-oxocyclopentyl)acetate.

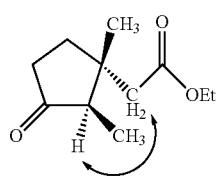

Example 2-3

Preparation of ethyl (1,2-dimethyl-3-methylenecyclopentyl)acetate (3: R=Et)

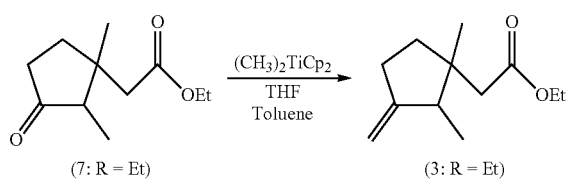

Air in a reactor equipped with a stirrer, a condenser, and a thermometer was purged with nitrogen. Then, to the reactor were added an ethyl (1,2-dimethyl-3-oxocyclopentyl)acetate (7: R=Et)[Diastereomer ratio=53.6 (1R*2 S* configuration, GC Retention time 14.40 minutes): 46.4 (1R*2R* configuration, GC Retention time 14.60 minutes)] (19.83 g: 0.100 mol, purity: 96.1%) thus obtained in Example 2-2 and tetrahydrofuran (THF) (50.0 g), and then the mixture was stirred at a liquid temperature of 20° C. to 25° C. Petasis reagent (tetrahydrofuran and toluene solution of 10 wt % dimethyltitanocene [(CH$_3$)$_2$TiCp$_2$, Cp: cyclopenta-1,3-dienyl], 249.8 g: 0.120 mol) separately prepared from titanocene chloride and methylmagnesium chloride was added to the mixture whose temperature was maintained at a liquid temperature of 20° C. to 25° C. over 15 minutes. After the completion of the addition, the mixture was stirred at a liquid temperature of 60° C. to 65° C. for 16 hours, and then, a saturated aqueous sodium bicarbonate solution (50.0 g) and methanol (5.0 g) were added to the reaction mixture in this order, and stirred at a liquid temperature of 20° C. to 25° C. for one hour. After the completion of the stirring, n-hexane (350.0 g) was added, and stirred at a reaction mixture temperature of 20° C. to 25° C. for six hours, and the reaction mixture was filtered to separate the precipitated solids and the filtrate. Subsequently, the filtrate was washed with a saturated sodium chloride solution (100.0 g). The solvent was removed from the washed filtrate at a reduced pressure to obtain the crude product comprising ethyl (1,2-dimethyl-3-methylenecyclopentyl)acetate (3: R=Et) (17.27 g: 0.088 mol, yield 88.0%, purity 76.9%).

It was verified from the gas chromatography analysis that ethyl (1,2-dimethyl-3-methylenecyclopentyl)acetate (3: R=Et) thus prepared has two types of diastereomers [Diastereomer product ratio=49.4 (GC Retention time 12.85 minutes): 50.6 (GC Retention time 13.02 minutes)] at Retention time 12.85 minutes and Retention time 13.02 minutes, respectively. The above yields of ethyl (1,2-dimethyl-3-methylenecyclopentyl)acetate (3: R=Et) are represented as a mixture of the two types of diastereomers.

In order to determine the relative configuration of the two types of diastereomers of ethyl (1,2-dimethyl-3-methylenecyclopentyl)acetate (3: R=Et) thus prepared, the two dimensional NOESY spectrum was measured, and the Nuclear Overhauser effect (NOE) was verified. The results are shown below. Note that, the NOE is indicated by both arrows.

It is thought that the diastereomer detected at the GC Retention time 12.85 minutes is the following ethyl (1R*, 2R*)-(1,2-dimethyl-3-methylenecyclopentyl)acetate, and

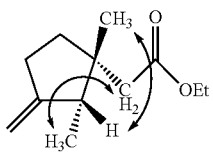

the diastereomer detected at the GC Retention time 13.02 minutes is the following ethyl (1R*,2S*)-(1,2-dimethyl-3-methylenecyclopentyl)acetate.

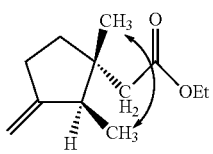

The crude product comprising ethyl (1,2-dimethyl-3-methylenecyclopentyl)acetate (3: R=Et) thus prepared was purified by silica gel column chromatography, and separated into Fraction A and Fraction B having different diastereomer ratios with each other, as shown below.

Fraction A: (7.99 g: 0.041 mol, yield 40.7%, purity 97.7%) Diastereomer ratio=57.8 (1R*2R* configuration, GC Retention time 12.85 minutes): 42.2 (1R*2 S* configuration, GC Retention time 13.02 minutes)]

Fraction B: (8.83 g: 0.045 mol, yield 45.2%, purity 91.6%) Diastereomer ratio=36.8 (1R*2R* configuration, GC Retention time 12.85 minutes): 63.2 (1R*2 S* configuration, GC Retention time 13.02 minutes)]

The following are various spectrum data of Fraction A and Fraction B thus prepared, respectively.

Fraction A

Nuclear magnetic resonance spectrum: $^1$H-NMR (600 MHz, CDCl$_3$): δ 0.77 (1.3H, s), 0.93 (1.7H, d, J=7.2 Hz), 0.94 (1.3H, d, J=7.2 Hz), 1.13 (1.7H, s), 1.25 (1.7H, t, J=7.2 Hz), 1.26 (1.3H, t, J=7.2 Hz), 1.37 (0.6H, dt, J=17.4, 7.8 Hz), 1.65-1.68 (0.8H, m), 1.91 (0.6H, ddd, J=13.2, 8.7, 3.8 Hz), 1.99 (0.6H, d, J=13.8 Hz), 2.02 (0.6H, d, J=13.8 Hz), 2.10-2.17 (1H, m), 2.20 (0.4H, d, J=13.8 Hz), 2.28-2.43 (2.4H, m), 4.09-4.15 (2H, m), 4.77-4.78 (1H, m), 4.86-4.87 (1H, m) ppm. $^{13}$C-NMR (150 MHz, CDCl$_3$): δ 11.64, 11.94, 14.45, 18.74, 24.71, 29.03, 29.24, 35.26, 36.47, 38.22, 43.24, 43.72, 45.33, 48.14, 50.52, 60.10, 60.15, 105.16, 105.40, 156.06, 156.34, 172.57, 173.16 ppm.

Mass spectrum EI (70 ev) GC Retention time 12.85 minutes: m/z 196 (M$^+$), 181, 151, 123, 108, 93, 81, 79, 67, 53, 41, 29. GC Retention time 13.02 minutes: m/z 196 (M$^+$), 181, 151, 123, 108, 93, 81, 79, 67, 53, 41, 29.

Infrared absorption spectrum (D-ATR): ν (cm$^{-1}$) 880, 1036, 1095, 1120, 1200, 1236, 1263, 1324, 1368, 1453, 1655, 1733, 2872, 2938, 2963, 3074.

Fraction B

Nuclear magnetic resonance spectrum: $^1$H-NMR (600 MHz, CDCl$_3$): δ 0.77 (1.8H, s), 0.93 (1.2H, d, J=7.2 Hz), 0.94 (1.8H, d, J=7.2 Hz), 1.13 (1.2H, s), 1.25 (1.2H, t, J=7.2 Hz), 126 (1.8H, t, J=7.2 Hz), 1.37 (0.4H, dt, J=17.4, 7.8 Hz), 1.65-1.68 (1.2H, m), 1.91 (0.4H, ddd, J=13.2, 8.7, 3.8 Hz), 1.99 (0.4H, d, J=13.8 Hz), 2.02 (0.4H, d, J=13.8 Hz), 2.10-2.17 (1H, m), 2.20 (0.6H, d, J=13.8 Hz), 2.28-2.43 (2.6H, m), 4.09-4.15 (2H, m), 4.77-4.78 (1H, m), 4.86-4.87 (1H, m) ppm. $^{13}$C-NMR (150 MHz, CDCl$_3$): δ 11.64, 11.94, 14.45, 18.74, 24.71, 29.03, 29.24, 35.26, 36.47, 38.22, 43.24, 43.72, 45.33, 48.14, 50.52, 60.10, 60.15, 105.16, 105.40, 156.06, 156.34, 172.57, 173.16 ppm.

Mass spectrum EI (70 ev) GC Retention time 12.85 minutes: m/z 196 (M$^+$), 181, 151, 123, 108, 93, 81, 79, 67, 53, 41, 29. GC Retention time 13.02 minutes: m/z 196 (M$^+$), 181, 151, 123, 108, 93, 81, 79, 67, 53, 41, 29.

Infrared absorption spectrum (D-ATR): ν (cm$^{-1}$) 880, 1036, 1095, 1120, 1200, 1236, 1263, 1324, 1368, 1453, 1655, 1733, 2872, 2938, 2963, 3074.

Example 3

The following Example 3-1 to Example 3-3 describe processes for preparing (1,2-dimethyl-3-methylenecyclopentyl)acetaldehyde (4) from (1,2-dimethyl-3-methylenecyclopentyl) acetate (3), as shown in the following reaction formula.

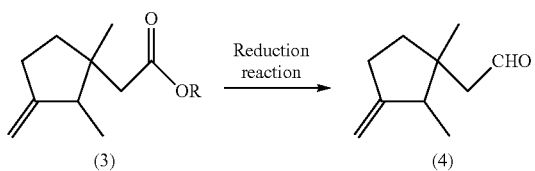

Example 3-1

Preparation of (1,2-dimethyl-3-methylenecyclopentyl)acetaldehyde (4)

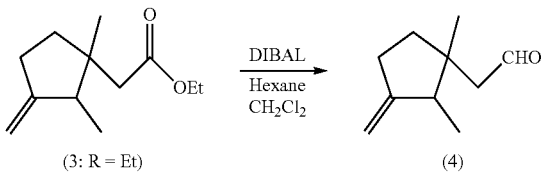

Air in a reactor equipped with a stirrer, a condenser, and a thermometer was purged with nitrogen. Then, to the reactor were added ethyl (1,2-dimethyl-3-methylenecyclopentyl)acetate (3: R=Et)[Diastereomer ratio=57.8 (1R*2R* configuration, GC Retention time 12.85 minutes): 42.2 (1R*2 S* configuration, GC Retention time 13.02 minutes)] (9.81 g: 0.050 mol, purity: 97.7%) obtained in Example 2-3 and methylene chloride (CH$_2$Cl$_2$) (380.0 g), and then the mixture was stirred at a liquid temperature of −65° C. to −75° C. A solution of 1M diisobutylaluminum hydride (DIBAL) (55.0 ml: 0.055 mol) in n-hexane was added dropwise to the mixture whose temperature was maintained at a liquid temperature of −60° C. to −70° C. over one hour. After the addition, the mixture was stirred for two hours at a liquid temperature of −60° C. to −65° C. After the completion of the stirring, ethanol (4.5 g) was added dropwise to the reaction mixture to quench the reaction. After the quenching of the reaction, a saturated aqueous potassium sodium tartrate solution (230.0 g) was added, and stirred at a liquid temperature of 20° C. to 25° C. for 12 hours, and then extracted with diethyl ether (200.0 g), and the reaction mixture was separated into an organic layer and an aqueous layer. The obtained organic layer was washed with a saturated aqueous sodium chloride solution (250.0 g). The solvent was removed from the washed organic layer at a reduced pressure to obtain (1,2-dimethyl-3-methylenecyclopentyl)acetaldehyde (4) (6.63 g: 0.044 mol, yield 87.1%, purity 79.3%).

It was verified from the gas chromatography analysis that (1,2-dimethyl-3-methylenecyclopentyl)acetaldehyde (4) thus prepared has two types of diastereomers [Diastereomer product ratio=58.1 (GC Retention time 10.18 minutes): 41.9 (GC Retention time 10.34 minutes)] at Retention times 10.18 minute and Retention time 10.34 minutes, respectively. The above yields of (1,2-dimethyl-3-methylenecyclopentyl)acetaldehyde (4) are represented as a mixture of the two types of diastereomers.

From the results described in Non-Patent Literature 2 and 3, it was verified that with regards to the relative configuration of the two types of diastereomers of (1,2-dimethyl-3-methylenecyclopentyl)acetaldehyde (4) thus prepared, the diastereomer detected at the GC Retention time 10.18 minutes has the (1R*2R*) configuration, and the diastereomer detected at the GC Retention time 10.34 minutes has the (1R*,2S*) configuration.

The crude product comprising (1,2-dimethyl-3-methylenecyclopentyl)acetaldehyde (4) thus prepared was purified by silica gel column chromatography, and separated into Fraction C and Fraction D having different diastereomer ratios with each other, as shown below.

Fraction C: (3.04 g: 0.020 mol, yield 40.0%, purity 91.2%)
Diastereomer ratio=70.3 (1R*2R* configuration, GC Retention time 10.18 minutes): 29.7 (1R*2 S* configuration, GC Retention time 10.34 minutes)]
Fraction D: (2.43 g: 0.016 mol, yield 31.9%, purity 91.5%)
Diastereomer ratio=36.8 (1R*2R* configuration, GC Retention time 10.18 minutes): 63.2 (1R*2 S* configuration, GC Retention time 13.34 minutes)]

The following are various spectrum data of Fraction C and Fraction D thus prepared, respectively.

Fraction C
Nuclear magnetic resonance spectrum: $^1$H-NMR (600 MHz, CDCl$_3$): δ 0.82 (0.9H, s), 0.95 (0.9H, d, J=6.6 Hz), 0.96 (2.1H, d, J=7.2 Hz), 1.19 (2.1H, s), 1.48 (0.7H, dt, J=16.8, 6.5 Hz), 1.63-1.69 (0.3H, m), 1.72-1.76 (0.3H, m), 1.86 (0.7H, ddd, J=13.2, 8.7, 3.3 Hz), 2.07-2.12 (2.1H, m), 2.13-2.18 (0.3H, m), 2.27 (0.3H, dd, J=14.4, 2.4 Hz), 2.30-2.4 (1.0H, m), 2.42-2.48 (1.0H, m), 2.51 (0.3H, dd, J=15.0, 3.3 Hz), 4.80 (1.0H, q, J=2.4 Hz), 4.88 (0.7H, q, J=2.4 Hz), 4.90 (0.3H, q, J=2.4 Hz), 9.84 (0.7H, t, J=3.0 Hz), 9.87 (0.3H, dd, J=3.6, 2.7 Hz) ppm. $^{13}$C-NMR (150 MHz, CDCl$_3$): δ 11.70, 12.08, 19.10, 25.17, 28.97, 29.28, 35.67, 36.51, 43.11, 43.66, 47.46, 48.69, 50.44, 54.42, 105.61, 105.82, 155.04, 155.69, 203.34, 203.93 ppm.

Mass spectrum EI (70 ev) GC Retention time 10.18 minutes: m/z 152 (M$^+$), 137, 119, 109, 108, 95, 93, 91, 81, 79, 67, 55, 53, 41, 39, 29. GC Retention time 10.34 minutes: m/z 152 (M$^+$), 137, 119, 108, 93, 91, 81, 79, 77, 67, 55, 53, 41, 39, 29.

Infrared absorption spectrum (D-ATR): ν (cm$^{-1}$) 881, 1048, 1106, 1147, 1297, 1382, 1407, 1454, 1655, 1722, 2731, 2840, 2872, 2960, 3074.

Fraction D
Nuclear magnetic resonance spectrum: $^1$H-NMR (600 MHz, CDCl$_3$): δ 0.82 (1.8H, s), 0.95 (1.8H, d, J=6.6 Hz), 0.96 (1.2H, d, J=7.2 Hz), 1.19 (1.2H, s), 1.48 (0.4H, dt, J=16.8, 6.5 Hz), 1.63-1.69 (0.6H, m), 1.72-1.76 (0.6H, m), 1.86 (0.4H, ddd, J=13.2, 8.7, 3.3 Hz), 2.07-2.12 (1.2H, m), 2.13-2.18 (0.6H, m), 2.27 (0.6H, dd, J=14.4, 2.4 Hz), 2.30-2.4 (1.0H, m), 2.42-2.48 (1.0H, m), 2.51 (0.6H, dd, J=15.0, 3.3 Hz), 4.80 (1.0H, q, J=2.4 Hz), 4.88 (0.4H, q, J=2.4 Hz), 4.90 (0.6H, q, J=2.4 Hz), 9.84 (0.4H, t, J=3.0 Hz), 9.87 (0.6H, dd, J=3.6, 2.7 Hz) ppm. $^{13}$C-NMR (150 MHz, CDCl$_3$): δ 11.70, 12.08, 19.10, 25.17, 28.97, 29.28, 35.67, 36.51, 43.11, 43.66, 47.46, 48.69, 50.44, 54.42, 105.61, 105.82, 155.04, 155.69, 203.34, 203.93 ppm.

Mass spectrum EI (70 ev) GC Retention time 10.18 minutes: m/z 152 (M$^+$), 137, 119, 109, 108, 95, 93, 91, 81, 79, 67, 55, 53, 41, 39, 29. GC Retention time 10.34 minutes: m/z 152 (M$^+$), 137, 119, 108, 93, 91, 81, 79, 77, 67, 55, 53, 41, 39, 29

Infrared absorption spectrum (D-ATR): ν (cm$^{-1}$) 879, 1048, 1107, 1149, 1297, 1381, 1406, 1436, 1655, 1721, 2730, 2840, 2872, 2962, 3074.

Example 3-2

Preparation of 2-(1,2-dimethyl-3-methylenecyclopentyl)ethyl alcohol (8)

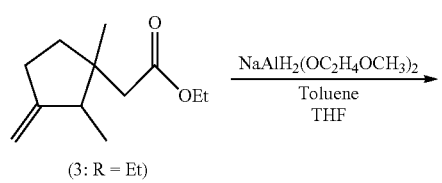

(3: R = Et)

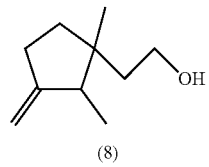

(8)

Air in a reactor equipped with a stirrer, a condenser, and a thermometer was purged with nitrogen. Then, to the reactor were added ethyl (1,2-dimethyl-3-methylenecyclopentyl)acetate (3: R=Et)[Diastereomer ratio=57.8 (1R*2R* configuration, GC Retention time 12.85 minutes): 42.2 (1R*2 S* configuration, GC Retention time 13.02 minutes)] (19.63 g: 0.100 mol, purity: 97.7%) obtained in Example 2-3 and tetrahydrofuran (450.0 g), and then the mixture was stirred at a liquid temperature of 0° C. to 5° C. A 70 wt % sodium bis(2-methoxyethoxy)aluminum hydride solution (NaAlH$_2$(OC$_2$H$_4$OCH$_3$)$_2$) (43.32 g: 0.150 mol) in toluene was added dropwise to the mixture whose temperature was maintained at a liquid temperature of 0° C. to 5° C. over two hours. After the completion of the dropwise addition, the reaction mixture was stirred at a liquid temperature of 20° C. to 25° C. for three hours. After the completion of the stirring, a liquid temperature of the reaction mixture was cooled to 5° C. or less, and then, an aqueous 10 wt % sodium hydroxide solution (120.0 g) was added dropwise to the reaction mixture at a liquid temperature of 5° C. to 15° C. After the completion of the dropwise addition, the reaction mixture was stirred at a liquid temperature of 35° C. to 40° C. for one hour. After the completion of the stirring, the reaction mixture was separated into an organic layer and an aqueous layer, the obtained organic layer was washed twice with an aqueous 10 wt % sodium chloride solution (300 g). The solvent was removed from the washed organic layer at a reduced pressure to obtain a crude product comprising 2-(1,2-dimethyl-3-methylenecyclopentyl)ethyl alcohol (8) (15.02 g: 0.097 mol, yield 97.4%, purity 88.1%).

It was verified from the gas chromatography analysis that 2-(1,2-dimethyl-3-methylenecyclopentyl)ethyl alcohol (8) thus prepared has two types of diastereomers [Diastereomer product ratio=64.5 (GC Retention time 11.67 minutes): 35.5 (GC Retention time 11.84 minutes)] at Retention time 11.67 minutes and Retention time 11.84 minutes, respectively. The above yields of 2-(1,2-dimethyl-3-methylenecyclopentyl) ethyl alcohol (8) are represented as a mixture of the two types of diastereomers.

From the results described in Non-Patent Literature 2 and 3, it was verified that with regards to the relative configuration of the two types of diastereomers of 2-(1,2-dimethyl-3-methylenecyclopentyl)ethyl alcohol (8) thus prepared, the diastereomer detected at the GC Retention time 11.67 minutes has the (1R*2R*) configuration, and the diastereomer detected at the GC Retention time 11.84 minutes has the (1R*,2S*) configuration.

The crude product comprising 2-(1,2-dimethyl-3-methylenecyclopentyl)ethyl alcohol (8) thus prepared was purified by silica gel column chromatography, and separated into Fraction E and Fraction F having different diastereomer ratios with each other, as shown below.

Fraction E: (10.09 g: 0.065 mol, yield 65.4%, purity 96.9%) Diastereomer ratio=77.1 (1R*2R* configuration, GC Retention time 11.67 minutes): 22.9 (1R*2 S* configuration, GC Retention time 11.84 minutes)]

Fraction F: (4.50 g: 0.029 mol, yield 29.2%, purity 98.3%) Diastereomer ratio=19.5 (1R*2R* configuration, GC Retention time 11.67 minutes): 80.5 (1R*2 S* configuration, GC Retention time 11.84 minutes)]

The following are various spectrum data of Fraction E and Fraction F thus prepared, respectively.

Fraction E

Nuclear magnetic resonance spectrum: $^1$H-NMR (600 MHz, DMSO-d$_6$): δ 0.60 (0.6H, s), 0.86 (0.6H, d, J=6.6 Hz), 0.88 (2.4H, d, J=6.6 Hz), 0.94 (2.4H, s), 1.16-12.0 (1.6H, m), 123 (0.8H, dt, J=12.6, 9.0 Hz), 1.36 (0.2H, ddd, J=12.6, 9.0, 6.6 Hz), 1.42-1.49 (0.4H, m), 1.61 (0.2H, ddd, J=13.8, 9.3, 6.0 Hz), 1.71 (0.8H, ddd, J=12.6, 8.4, 3.8 Hz), 1.93-2.01 (1.0H, m), 2.19-2.26 (1.0H, m), 2.27-2.34 (1.0H, m), 3.42 (1.6H, td, J=7.5, 4.8 Hz), 3.45-3.52 (0.4H, m), 4.24 (0.8H, t, J=5.1 Hz), 4.29 (0.2H, t, J=4.8 Hz), 4.72-4.75 (1.0H, m), 4.79-4.80 (0.8H, m), 4.81-4.82 (0.2H, m) ppm. $^{13}$C-NMR (150 MHz, DMSO-d$_6$): δ 11.83, 11.88, 18.43, 24.64, 28.79, 28.99, 34.54, 35.51, 35.91, 42.24, 42.33, 43.25, 48.01, 50.08, 57.73, 57.86, 104.59, 104.62, 156.22, 156.79 ppm.

Mass spectrum EI (70 ev) GC Retention time 11.67 minutes: m/z 154 (M$^+$), 139, 125, 121, 110, 109, 95, 93, 81, 79, 77, 69, 67, 55, 53, 41, 29. GC Retention time 11.84 minutes: m/z 154 (M$^+$), 139, 125, 121, 110, 109, 95, 93, 81, 79, 77, 69, 67, 55, 53, 41, 29. Infrared absorption spectrum (ATR): ν (cm$^{-1}$) 878, 938, 1000, 1037, 1106, 1373, 1406, 1453, 1655, 1726, 1742, 2871, 2938, 2958, 3073, 3337.

Fraction F

Nuclear magnetic resonance spectrum: $^1$H-NMR (600 MHz, DMSO-d$_6$): δ 0.60 (2.4H, s), 0.86 (2.4H, d, J=6.6 Hz), 0.88 (0.6H, d, J=6.6 Hz), 0.94 (0.6H, s), 1.16-1.20 (0.4H, m), 1.23 (0.2H, dt, J=12.6, 9.0 Hz), 1.36 (0.8H, ddd, J=12.6, 9.0, 6.6 Hz), 1.42-1.49 (1.6H, m), 1.61 (0.8H, ddd, J=13.8, 9.3, 6.0 Hz), 1.71 (0.2H, ddd, J=12.6, 8.4, 3.8 Hz), 1.93-2.01 (1.0H, m), 2.19-2.26 (1.0H, m), 2.27-2.34 (1.0H, m), 3.42 (0.4H, td, J=7.5, 4.8 Hz), 3.45-3.52 (1.6H, m), 4.24 (0.2H, t, J=5.1 Hz), 4.29 (0.8H, t, J=4.8 Hz), 4.72-4.75 (1.0H, m), 4.79-4.80 (0.2H, m), 4.81-4.82 (0.8H, m) ppm. $^{13}$C-NMR (150 MHz, DMSO-d$_6$): δ 11.83, 11.89, 18.43, 24.64, 28.79, 28.99, 34.54, 35.50, 35.91, 42.24, 42.33, 43.25, 48.01, 50.08, 57.73, 57.86, 104.59, 104.62, 156.22, 156.79 ppm.

Mass spectrum EI (70 ev) GC Retention time 11.67 minutes: m/z 154 (M$^+$), 139, 125, 121, 110, 109, 95, 93, 81, 79, 77, 69, 67, 55, 53, 41, 29. GC Retention time 11.84 minutes: m/z 154 (M$^+$), 139, 125, 121, 110, 109, 95, 93, 81, 79, 77, 69, 67, 55, 53, 41, 29.

Infrared absorption spectrum (ATR): ν (cm$^{-1}$) 876, 939, 1007, 1036, 1109, 1379, 1434, 1453, 1655, 1726, 2872, 2938, 2960, 3073, 3336.

Example 3-3

Preparation of (1,2-dimethyl-3-methylenecyclopentyl)acetaldehyde (4)

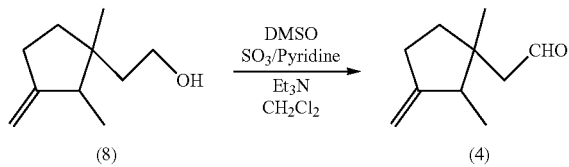

Air in a reactor equipped with a stirrer, a condenser, and a thermometer was purged with nitrogen. Then, to the reactor were added 2-(1,2-dimethyl-3-methylenecyclopentyl)ethyl alcohol (8)[Diastereomer ratio=77.1 (1R*2R* configuration, GC Retention time 11.67 minutes): 22.9 (1R*2 S* configuration, GC Retention time 11.84 minutes)] obtained in Example 3-2 (7.71 g: 0.05 mol, purity: 96.9%), triethylamine (Et$_3$N) (25.30 g: 0.250 mol) and methylene chloride (CH$_2$Cl$_2$) (230.0 g), and then the mixture was stirred at a liquid temperature of 15° C. to 20° C. A solution of a sulfur trioxide pyridine complex (SO$_3$/pyridine) (23.87 g: 0.150 mol) in dimethyl sulfoxide (DMSO) (148.4 g: 1.900 mol) was added dropwise to the mixture whose temperature was maintained at a liquid temperature of 20° C. to 25° C. over two hours. After the completion of the dropwise addition, the reaction mixture was stirred at a liquid temperature of 20° C. to 25° C. for two hours. After the completion of the stirring, 5 wt % hydrochloric acid (200.0 g) was added dropwise to the reactor to quench the reaction. After the quenching of the reaction, the reaction mixture was extracted with methylene chloride (150.0 g), and the reaction mixture was separated into an organic layer and an aqueous layer. The obtained organic layer was washed with 5 wt % hydrochloric acid (200.0 g), water (100.0 g), an aqueous 5 wt % sodium bicarbonate solution (150.0 g) and with an aqueous 5 wt % sodium chloride solution (200.0 g) in this order. The solvent was removed from the washed organic layer at a reduced pressure, and the obtained crude product was purified by silica gel column chromatography to obtain (1,2-dimethyl-3-methylenecyclopentyl)acetaldehyde (4) (7.51 g: 0.049 mol, yield 98.7%, purity 92.0%).

(1,2-dimethyl-3-methylenecyclopentyl)acetaldehyde (4) was verified as having two types of diastereomers [Diastereomer product ratio=75.8 (1R*2R* configuration, GC Retention time 10.18 minutes): 24.2 (1R*2 S*configuration, GC Retention time 10.34 minutes)]in the same manner as Example 3-1. The above yields of (1,2-dimethyl-3-methylenecyclopentyl)acetaldehyde (4) are represented as a mixture of the two types of diastereomers.

The following are various spectrum data of (1,2-dimethyl-3-methylenecyclopentyl)acetaldehyde (4) thus prepared.

Nuclear magnetic resonance spectrum: $^1$H-NMR (500 MHz, CDCl$_3$): δ 0.81 (0.6H, s), 0.94 (0.6H, d, J=6.9 Hz), 0.94 (2.4H, d, J=6.9 Hz), 1.18 (2.4H, s), 1.47 (0.8H, dt, J=13.1, 9.6 Hz), 1.62-1.70 (0.2H, m), 1.73 (0.2H, ddd, J=12.2, 8.9, 3.0 Hz), 1.85 (0.8H, ddd, J=12.5, 8.9, 3.5 Hz), 2.06-2.18 (2.6H, m), 2.26 (0.2H, dd, J=14.6, 5.4 Hz), 2.18-2.39 (1H, m), 2.40-2.47 (1H, m), 2.50 (0.2H, dd, J=14.5, 3.5 Hz), 4.79 (1H, q, J=2.3 Hz), 4.86-4.89 (1H, m), 9.82 (0.8H, t, J=3.1 Hz), 9.86 (0.2H, dd, J=3.5, 2.7 Hz) ppm. $^{13}$C-NMR (150 MHz, CDCl$_3$): δ 11.50, 11.89, 18.89, 24.97, 28.77, 29.09, 35.47, 36.31, 42.92, 43.46, 47.26, 48.50, 50.25, 54.22, 105.42, 105.63, 154.84, 155.50, 203.14, 203.74 ppm.

Mass spectrum EI (70 ev) GC Retention time 10.18 minutes: m/z 152 (M$^+$), 137, 119, 109, 108, 95, 93, 91, 81, 79, 67, 55, 53, 41, 39, 29. GC Retention time 10.34 minutes: m/z 152 (M$^+$), 137, 119, 108, 93, 91, 81, 79, 77, 67, 55, 53, 41, 39, 29.

Infrared absorption spectrum (D-ATR): ν (cm$^{-1}$) 880, 1049, 1106, 1298, 1382, 1407, 1454, 1655, 1721, 2731, 2838, 2873, 2960, 3074.

Comparative Example

The following Comparative Example 1 describes a process for preparing ethyl (1,2-dimethyl-2-cyclopentenyl)acetate (2: R=Et) from the aforementioned 2,3-dimethyl-2-cyclopenten-1-ol (10) using the Johnson-Claisen rearrangement reaction described in Non-Patent Literature 4.

Comparative Example 1

Preparation of ethyl (1,2-dimethyl-2-cyclopentenyl)acetate (2: R=Et)

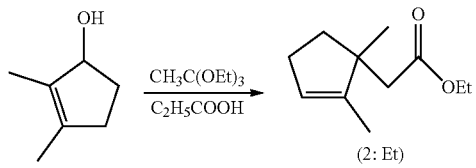

(2: Et)

Air in a reactor equipped with a stirrer, a condenser, a distillation tower, and a thermometer was purged with nitrogen. Then, to the reactor were added 2,3-dimethyl-2-cyclopenten-1-ol (8) (11.21 g: 0.100 mol, purity 93.6%), triethyl orthoacetate ($CH_3C(OEt)_3$) (81.12 g: 0.500 mol) and propionic acid (0.74 g: 0.010 mol), and the mixture was then stirred at a liquid temperature of 140° C. to 145° C. for 20 hours while distilling the refluxing ethanol off from a head of a fractional distillation tower. After the completion of the stirring, the reaction mixture was cooled to a liquid temperature of 20° C. to 25° C. The excess triethyl orthoacetate was removed from the reaction mixture at a reduced pressure, and the crude product was then purified by silica gel column chromatography to obtain ethyl (1,2-dimethyl-2-cyclopentenyl)acetate (2: R=Et) (7.49 g: 0.041 mol, yield 41.1%).

The $^1$H-NMR (Nuclear magnetic resonance spectrum) and mass spectrum data of the ethyl (1,2-dimethyl-2-cyclopentenyl)acetate (2: R=Et) thus prepared were the same as those determined in Example 1-1.

The yield of the ethyl (1,2-dimethyl-2-cyclopentenyl) acetate (2: R=Et) obtained in Comparative Example 1 was 41% which was lower than the yield of 83.0% in Example 1-1.

The invention claimed is:

1. A process for preparing a (1,2-dimethyl-3-methylenecyclopentyl)acetate compound of the following general formula (3):

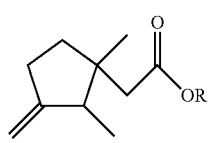

wherein R represents a linear or branched alkyl group having 1 to 4 carbon atoms,
the process comprising:
subjecting a haloacetaldehyde alkyl 2,3-dimethyl-2-cyclopentenyl acetal compound of the following general formula (1):

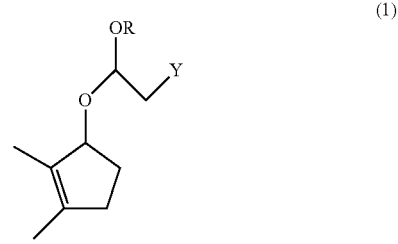

wherein R is as defined above, and Y represents a halogen atom,
to a dehydrohalogenation reaction in the presence of a base, followed by a rearrangement reaction to obtain a (1,2-dimethyl-2-cyclopentenyl)acetate compound of the following general formula (2):

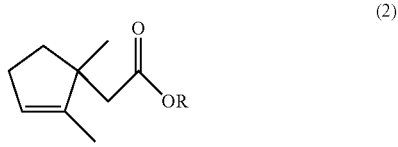

wherein R is as defined above, and
subjecting the (1,2-dimethyl-2-cyclopentenyl)acetate compound (2) to an epoxidation reaction, followed by an isomerization reaction, and then a methylenation reaction to obtain the (1,2-dimethyl-3-methylenecyclopentyl)acetate compound (3).

2. A process for preparing (1,2-dimethyl-3-methylenecyclopentyl)acetaldehyde of the following formula (4):

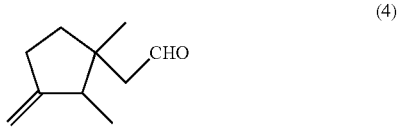

the process comprising:
the process for preparing the (1,2-dimethyl-3-methylenecyclopentyl)acetate compound (3) according to claim 1, and
converting an alkoxycarbonylmethyl group of the (1,2-dimethyl-3-methylenecyclopentyl)acetate compound (3) to a formylmethyl group to obtain (1,2-dimethyl-3-methylenecyclopentyl)acetaldehyde (4).

* * * * *